(12) United States Patent
Cushen et al.

(10) Patent No.: US 10,966,743 B2
(45) Date of Patent: Apr. 6, 2021

(54) SURGICAL INSTRUMENT HAVING CUTTING ASSEMBLY WITH GRIP

(71) Applicant: Stryker European Holdings I, LLC, Kalamazoo, MI (US)

(72) Inventors: Patrick Cushen, Graignamanagh (IE); Damian Michael Curtin, Tralee (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 204 days.

(21) Appl. No.: 16/087,743

(22) PCT Filed: Mar. 24, 2017

(86) PCT No.: PCT/IB2017/051723
§ 371 (c)(1),
(2) Date: Sep. 24, 2018

(87) PCT Pub. No.: WO2017/163226
PCT Pub. Date: Sep. 28, 2017

(65) Prior Publication Data
US 2020/0146702 A1    May 14, 2020

Related U.S. Application Data

(60) Provisional application No. 62/312,675, filed on Mar. 24, 2016.

(51) Int. Cl.
*A61B 17/32* (2006.01)
*A61B 17/00* (2006.01)

(52) U.S. Cl.
CPC ..... *A61B 17/32002* (2013.01); *A61B 2017/0046* (2013.01); *A61B 2017/00398* (2013.01);
(Continued)

(58) Field of Classification Search
CPC ............ A61B 10/0266; A61B 10/0275; A61B 10/0283; A61B 17/32002; A61B 2017/320032
See application file for complete search history.

(56) References Cited

U.S. PATENT DOCUMENTS 5,620,447 A * 4/1997 Smith ............... A61B 17/32002
604/22
5,685,838 A   11/1997 Peters et al.
(Continued)

FOREIGN PATENT DOCUMENTS

DE    202006006914 U1    6/2006
DE    102013111194 A1    4/2015
(Continued)

OTHER PUBLICATIONS

English language abstract and machine-assisted English translation for DE 20 2006 006 914 extracted from espacenet.com database on Oct. 25, 2018, 15 pages.
(Continued)

*Primary Examiner* — Wade Miles
(74) *Attorney, Agent, or Firm* — Howard & Howard Attorneys PLLC

(57) ABSTRACT

A cutting assembly for a surgical instrument. The cutting assembly comprises a tube assembly having an inner tube adapted to be rotated by a drive assembly, and an outer tube disposed over the inner tube. An aperture within each of the inner and outer tubes may define a cutting window adapted to be applied to a surgical site of a patient. A grip is coupled to the tube assembly and configured to be engaged by a hand of a user. A manually movable member for rotating the outer tube may be provided and rotated with an index finger or a thumb of the hand while the grip is engaged by a web of the hand. A web portion of the grip may be engaged by the web
(Continued)

of the hand without being engaged by a palm of the hand. Methods of gripping a cutting assembly are also disclosed.

14 Claims, 30 Drawing Sheets

(52) U.S. Cl.
CPC ............... *A61B 2017/00424* (2013.01); *A61B 2017/320032* (2013.01)

(56) References Cited

U.S. PATENT DOCUMENTS

| | | | |
|---|---|---|---|
| 5,916,231 | A | 6/1999 | Bays |
| 7,237,990 | B2 | 7/2007 | Deng |
| 7,247,161 | B2 | 7/2007 | Johnston et al. |
| 7,276,074 | B2 | 10/2007 | Adams et al. |
| 7,318,831 | B2 | 1/2008 | Alvarez et al. |
| 8,202,288 | B2 | 6/2012 | Adams et al. |
| 8,277,474 | B2 | 10/2012 | Norman et al. |
| 8,313,501 | B2 | 11/2012 | Miller et al. |
| 8,500,769 | B2 | 8/2013 | Deng |
| 8,920,419 | B2 | 12/2014 | Edwards et al. |
| 9,402,645 | B2 | 8/2016 | Norman et al. |
| 9,907,602 | B2 | 3/2018 | Fedenia et al. |
| 2005/0159767 | A1 | 7/2005 | Adams et al. |
| 2009/0270796 | A1 | 10/2009 | Perry et al. |
| 2012/0209255 | A1 | 8/2012 | Blocher et al. |
| 2013/0190759 | A1 | 7/2013 | Waaler et al. |
| 2013/0296910 | A1 | 11/2013 | Deng |
| 2014/0005700 | A1 | 1/2014 | Casey et al. |
| 2014/0155923 | A1* | 6/2014 | Edwards ............... A61B 90/90 606/170 |
| 2016/0302823 | A1 | 10/2016 | Nguyen et al. |
| 2017/0224403 | A1 | 8/2017 | Suzuki et al. |

FOREIGN PATENT DOCUMENTS

| | | |
|---|---|---|
| WO | 2014133664 A1 | 9/2014 |
| WO | 2015024600 A1 | 2/2015 |

OTHER PUBLICATIONS

Machine-assisted English language abstract and machine-assisted English translation for DE 10 2013 111 194 extracted from espacenet.com database on Oct. 25, 2018, 19 pages.

International Search Report for Application No. PCT/IB2017/051723 dated May 31, 2017, 3 pages.

Medtronic, "Healthcare Professionals Powered ENT Instruments-Handpieces and Accessories—Straightshot M4 Microbrider Webpage", www.medtronic.com/us-en/healthcare-professionals/products/ear-nose-throat/powered-ent-instr . . . , 2014-2018, 8 pages.

* cited by examiner

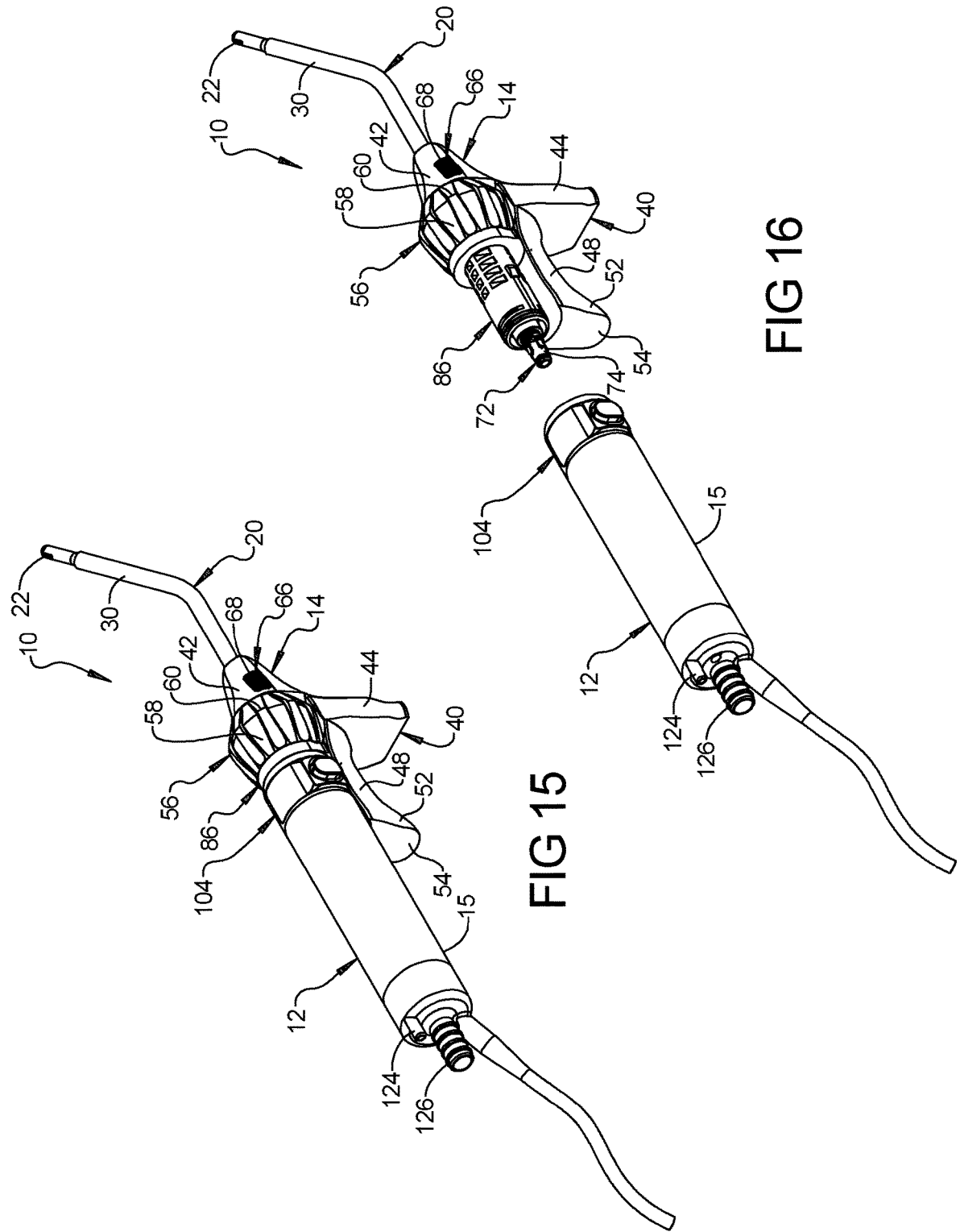

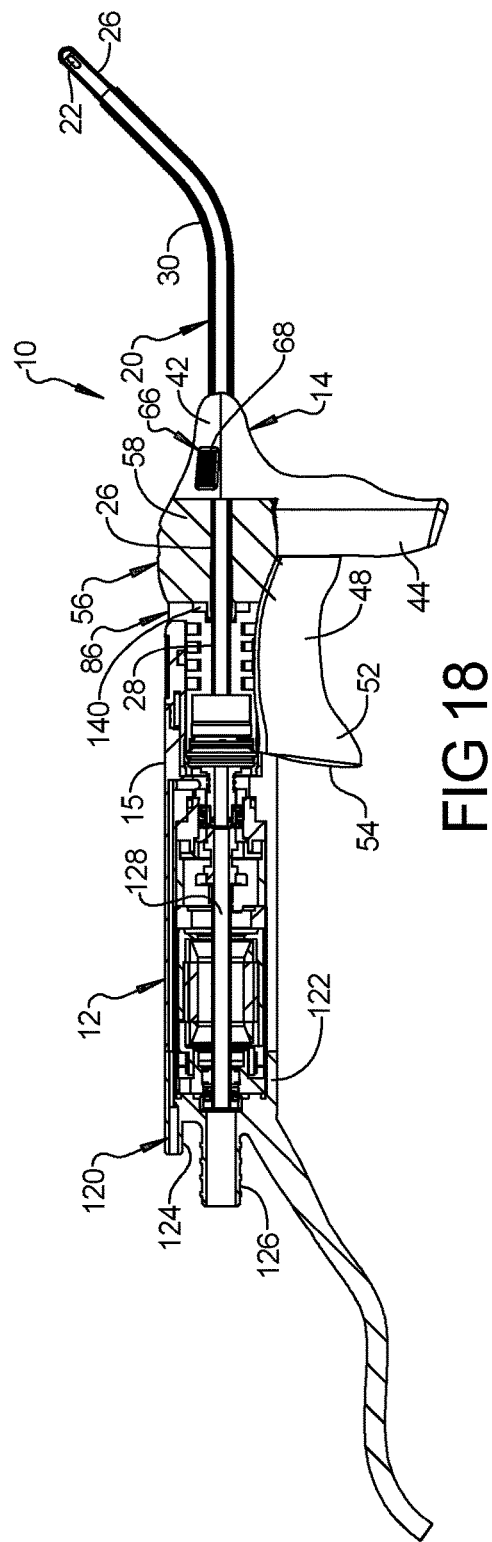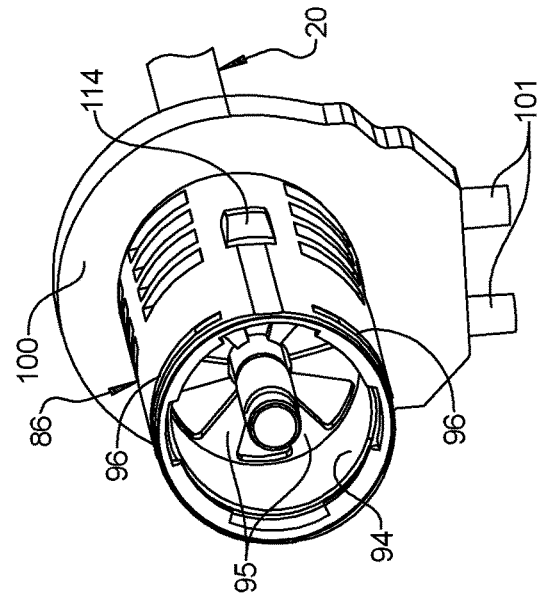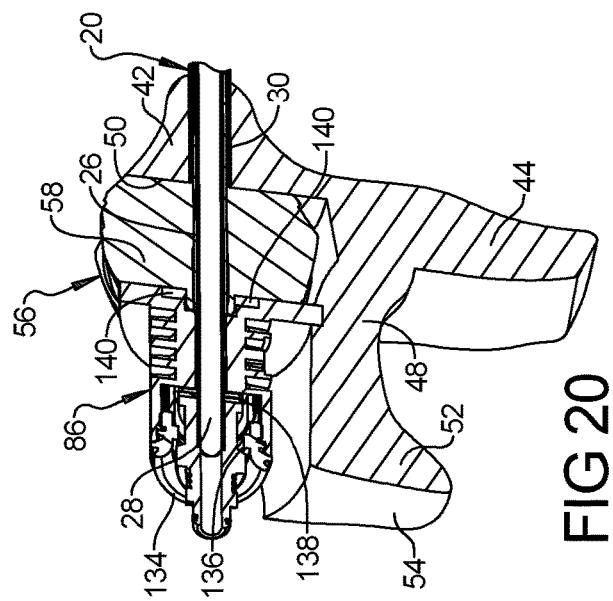

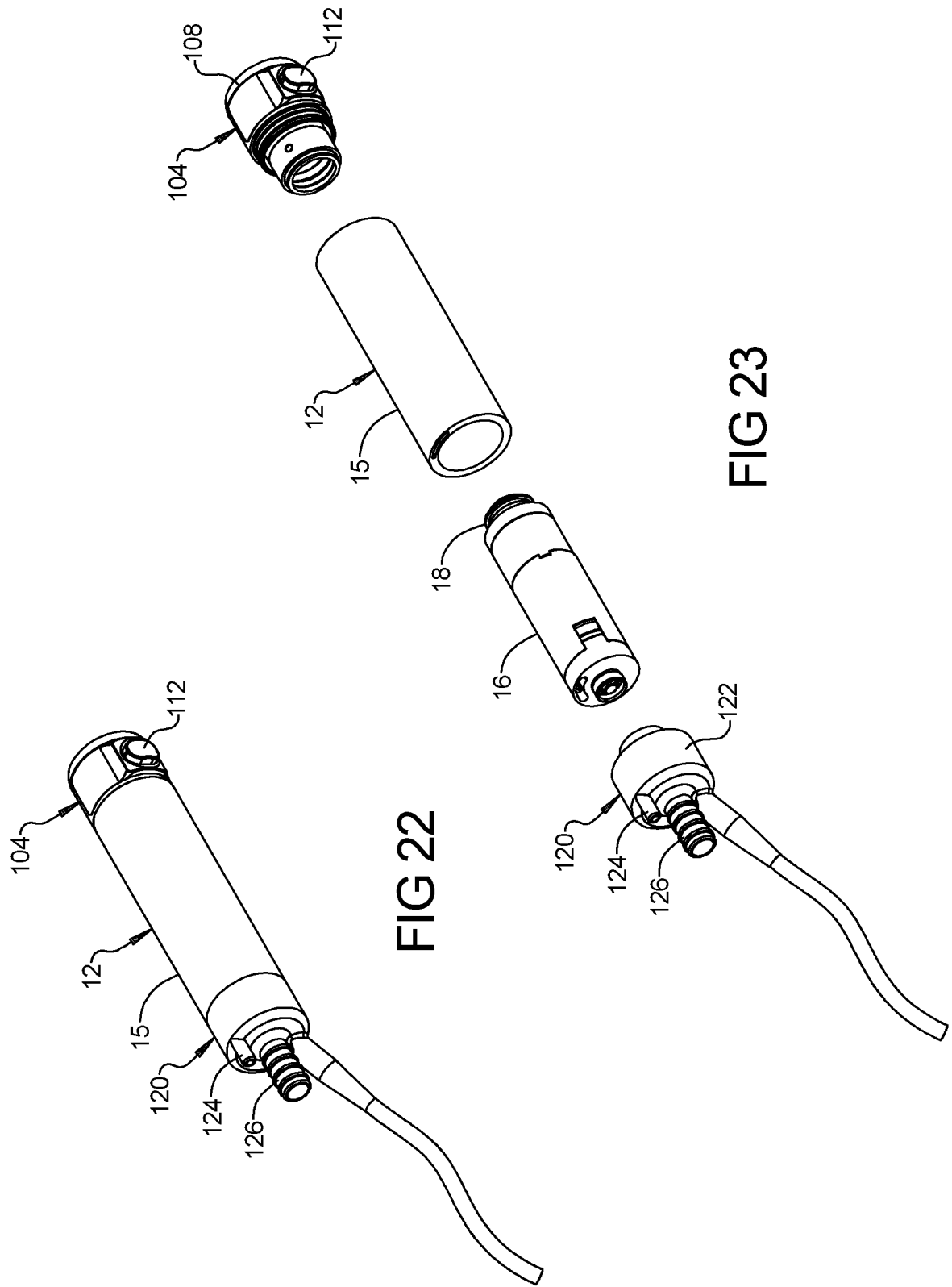

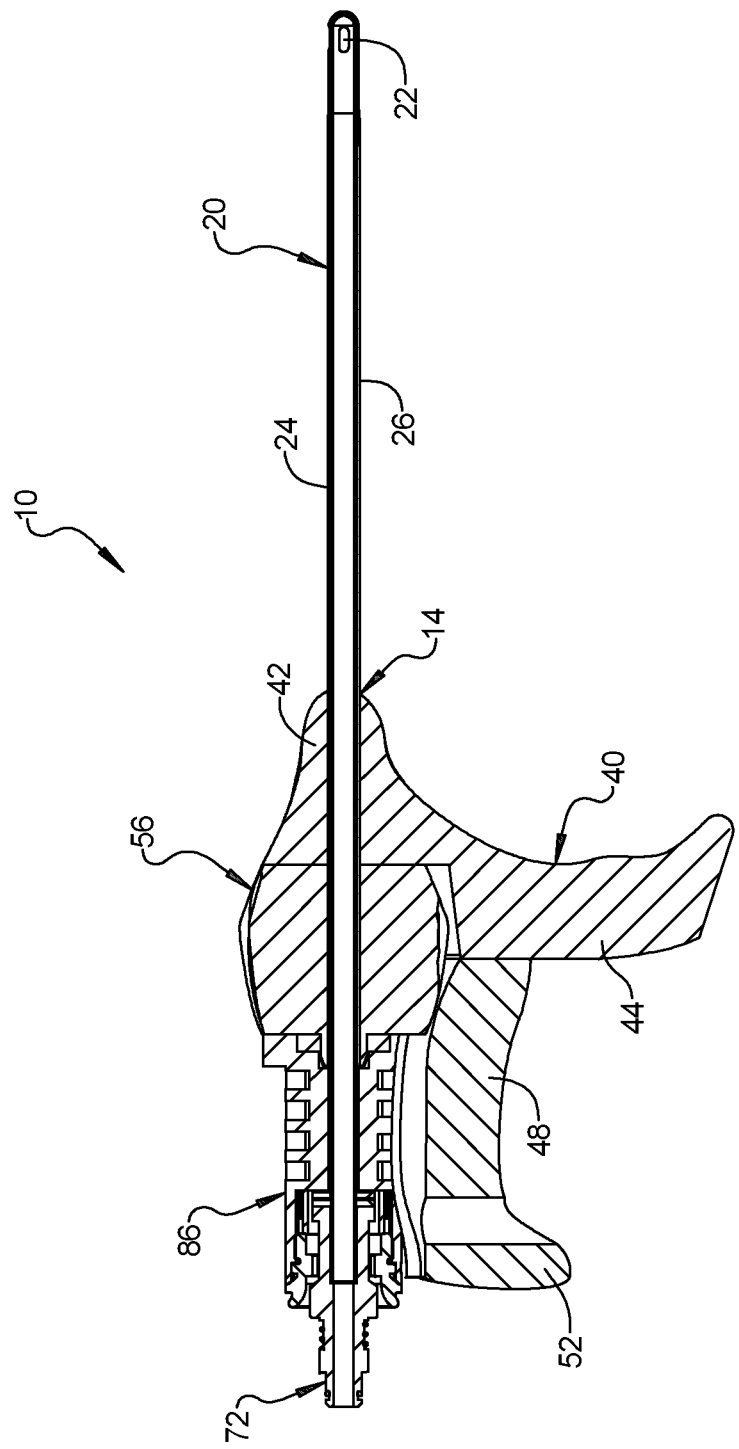

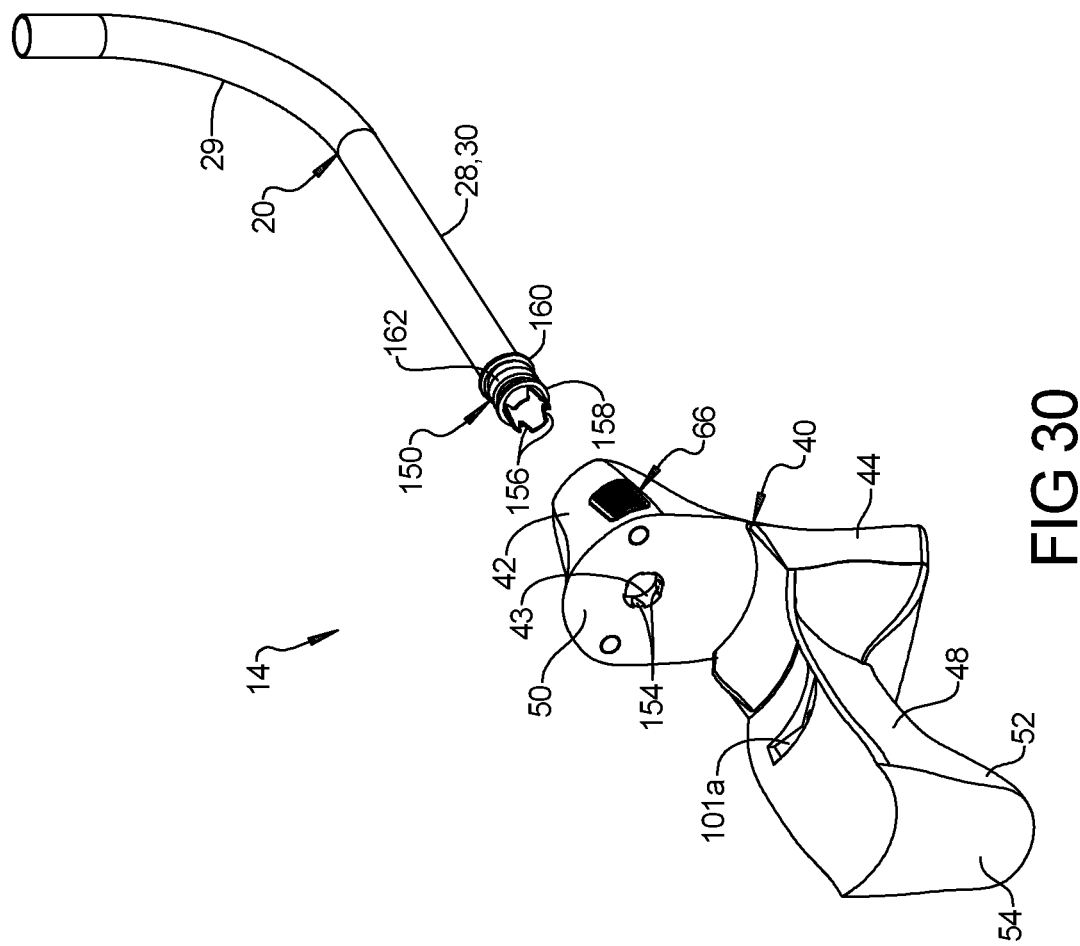

SURGICAL INSTRUMENT HAVING CUTTING ASSEMBLY WITH GRIP

CROSS-REFERENCE TO RELATED APPLICATIONS

This application is a U.S. National Stage of International Patent Application No. PCT/IB2017/051723, filed on Mar. 24, 2017, which claims priority to and all the benefits of U.S. Provisional Patent Application No. 62/312,675, filed on Mar. 24, 2016, the entire contents of which are hereby incorporated by reference.

TECHNICAL FIELD

The present invention relates generally to surgical instruments, and more particularly to a surgical instrument having a cutting assembly with a grip.

BACKGROUND

It is known that medical practitioners have found it useful to use surgical instruments to assist in the performance of surgical procedures. A surgical instrument is designed to be applied to a surgical site on the patient. The practitioner is able to position the surgical instrument at the site on the patient at which the instrument is to perform a medical or surgical procedure. Endoscopic surgical procedures are routinely performed in order to accomplish various surgical tasks. In endoscopic surgery the surgical site is may be accessed via small incisions called portals made in the patient, or through natural openings in the patient such as the nasal cavity in the case of sinus surgery. An endoscope, which is a device that allows medical personnel to view the surgical site, is inserted in one of the portals or nasal cavities. Surgical instruments used to perform specific surgical tasks are inserted together with the endoscope or though other portals. The surgeon views the surgical site through the endoscope to determine how to manipulate the surgical instruments in order to accomplish the surgical procedure. An advantage of performing endoscopic surgery is that it minimizes the amount of damage to surrounding tissues in order to access the surgical site and therefore the amount of the body that needs to heal after surgery. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery is enhanced by the development of powered surgical tools especially designed to perform endoscopic surgical procedures. One such tool, for example, is sold by the Applicant's Assignee under the trademark ESSx. This tool is in the form of a cylindrical handpiece designed to be held in the hand of the surgeon. Internal to the handpiece there is a motor. A front end of the handpiece is provided with a coupling assembly for releasably holding a cutting accessory. The types of cutting accessories that are attached to these handpieces include shavers and burs. Integral with the motor and coupling assembly is a mechanism for transmitting the rotary power developed by the motor to the cutting accessory. Often, handpieces are not comfortable to the user, and in many cases do not provide easy rotation of a cutting window of the cutting accessory. A surgical instrument designed to overcome one or more of the aforementioned disadvantages is desired.

SUMMARY

According to one exemplary embodiment of the present disclosure, a cutting assembly for a surgical instrument includes a drive assembly having a motor. The cutting assembly is configured to be removably coupled to the drive assembly of the surgical instrument. The cutting assembly comprises a tube assembly having a longitudinal axis defined between a distal end opposite a proximal end. A cutting window of the tube assembly is at the distal end and adapted to be applied to a surgical site of the patient. An inner tube of the tube assembly is adapted to be rotated by the drive assembly and comprises an inner tube aperture. The tube assembly further comprises an outer tube disposed over the inner tube and comprising an outer tube aperture. The inner tube and outer tube apertures define the cutting window of the tube assembly. The cutting assembly comprises a grip coupled to the tube assembly and configured to be engaged by a portion of a hand of a user. A manually movable member is coupled to the outer tube and adapted to be rotated by the user to rotate the outer tube aperture about the longitudinal axis. The manually movable member is adapted to be rotated with an index finger or a thumb of the hand while the grip is engaged by a web of the hand.

According to another exemplary embodiment of the present disclosure, a cutting assembly for a surgical instrument includes a drive assembly including a motor, and a housing coupled to the motor. The cutting assembly is configured to be removably coupled to the drive assembly of the surgical instrument. The cutting assembly comprises a tube assembly having an inner tube adapted to be rotated by the drive assembly, and an outer tube disposed over the inner tube. A grip is coupled to the tube assembly and configured to be engaged by a portion of a hand. The grip comprises a finger portion adapted to be engaged by an index finger or a secondary finger of the hand, and a web portion adapted to be engaged by the web of the hand without being engaged by the palm of the hand.

A method for gripping a cutting assembly with at least a portion of a hand of a user is provided. The cutting assembly includes a tube assembly having an inner tube rotatably disposed within an outer tube, a grip coupled to the tube assembly and comprising a finger portion and a web portion, and a manually movable member coupled to the outer tube of the tube assembly. The finger portion of the grip is engaged with a finger of the hand. The manually movable member is engaged with the finger, a thumb, or an index finger of the hand. The web portion of the grip is engaged with a web disposed between the thumb and the index finger of the hand. The manually movable member is moved with the thumb or the index finger to rotate the outer tube of the tube assembly while the web of the hand remains engaged with the web portion and the finger of the hand remains engaged with the finger portion. A drive assembly comprising a motor may be provided, and the drive assembly may be removably coupled to the cutting assembly.

BRIEF DESCRIPTION OF THE DRAWINGS

FIG. 15 is a perspective view of the surgical instrument of FIG. 1A.

FIG. 16 is a perspective view of the surgical instrument of FIG. 1A with the drive assembly disengaged from the cutting assembly.

FIG. 18 is an elevational view of the surgical instrument of FIG. 1A with a sectional view of the drive assembly and a portion of the cutting assembly.

FIG. 20 is a sectional perspective view of a portion of the cutting assembly of FIG. 18.

FIG. 21 is a perspective view of a connection hub of the cutting assembly.

FIG. 22 is a perspective view of the drive assembly.

FIG. 23 is an exploded view of the drive assembly of FIG. 22.

FIG. 29A is an elevational sectional view of a cutting assembly according to another exemplary embodiment of the present disclosure with the cutting assembly having a tube assembly with straight tubes.

FIG. 30 is an exploded view of a portion of a cutting assembly according to another exemplary embodiment of the present disclosure with the cutting assembly having a tube assembly adapted to be manually rotated relative to a grip.

DETAILED DESCRIPTION

Figure 1:
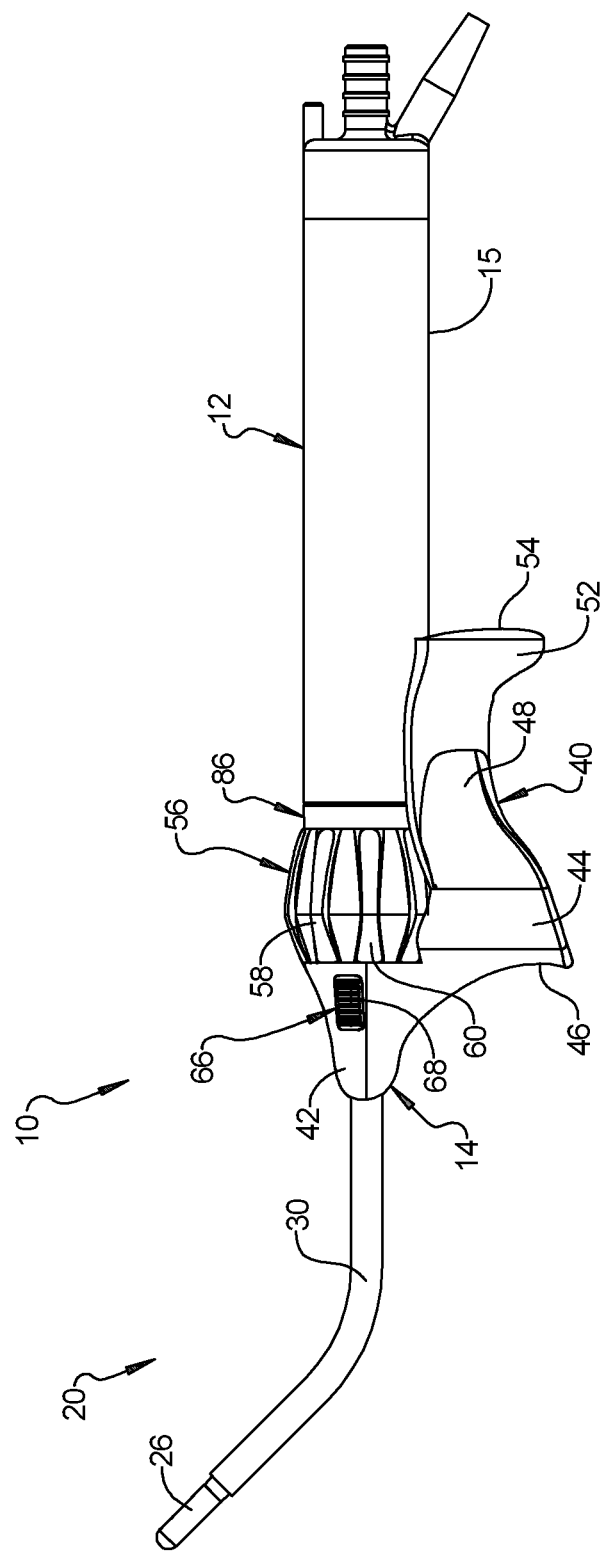
FIG. 1 is an elevational view of a surgical instrument according to an exemplary embodiment of the present disclosure.

Referring to FIG. 1, one embodiment of a surgical instrument 10, according to the present invention, is shown for use in a medical procedure for a patient (not shown). As illustrated, the surgical instrument 10 includes a drive assembly, generally indicated at 12, and a cutting assembly, generally indicated at 14, removably coupled to the drive assembly 12. The drive assembly 12 is used to rotate a portion of the cutting assembly 14 to remove tissue, bone, etc. from a surgical site of the patient. It should be appreciated that the surgical instrument 10 may be operated by a user (not shown) such as a surgeon.

Figure 17:
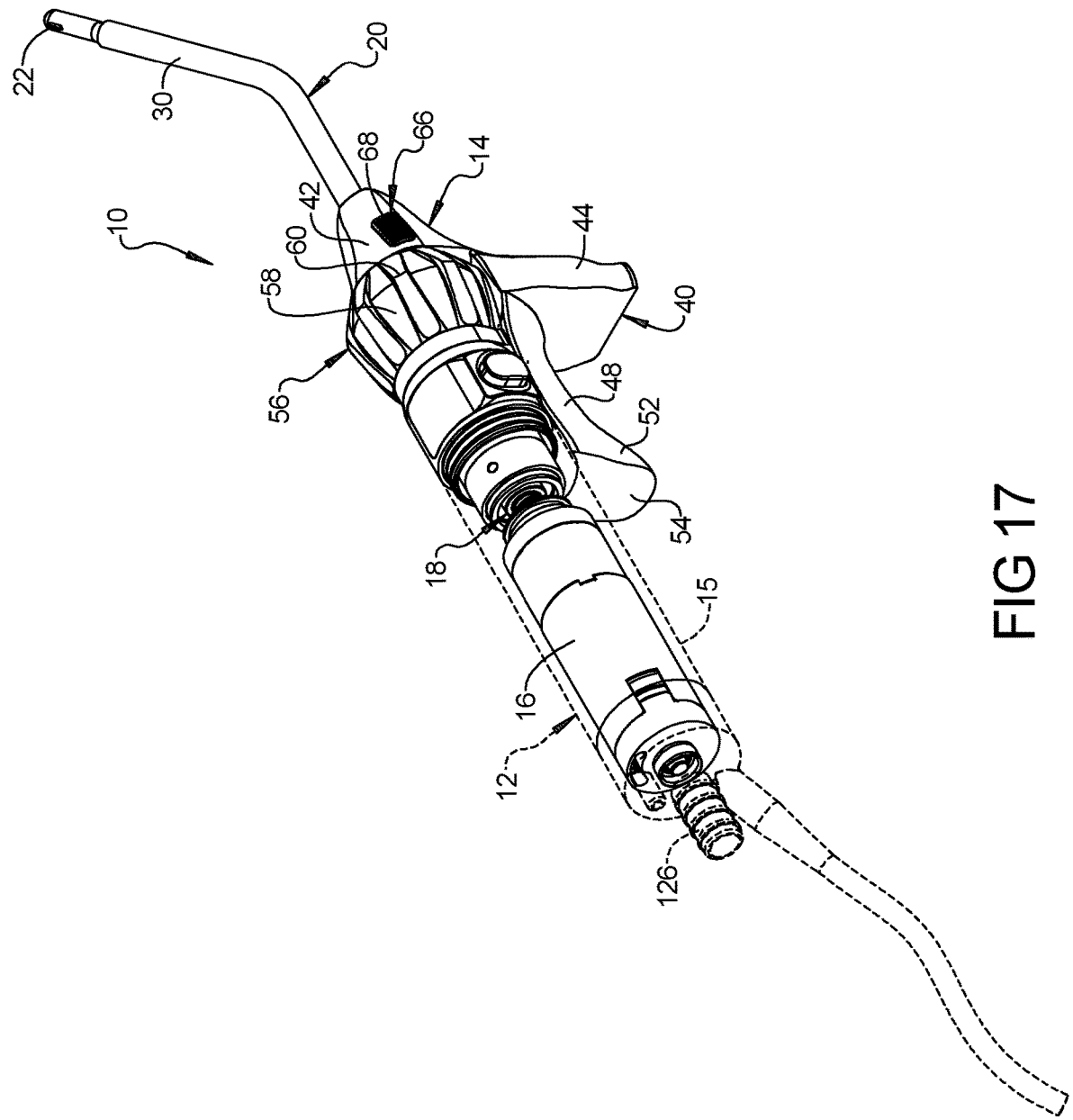
FIG. 17 is a perspective view of the surgical instrument of FIG. 1A, with a housing of the drive assembly is shown in phantom.
Figure 19:
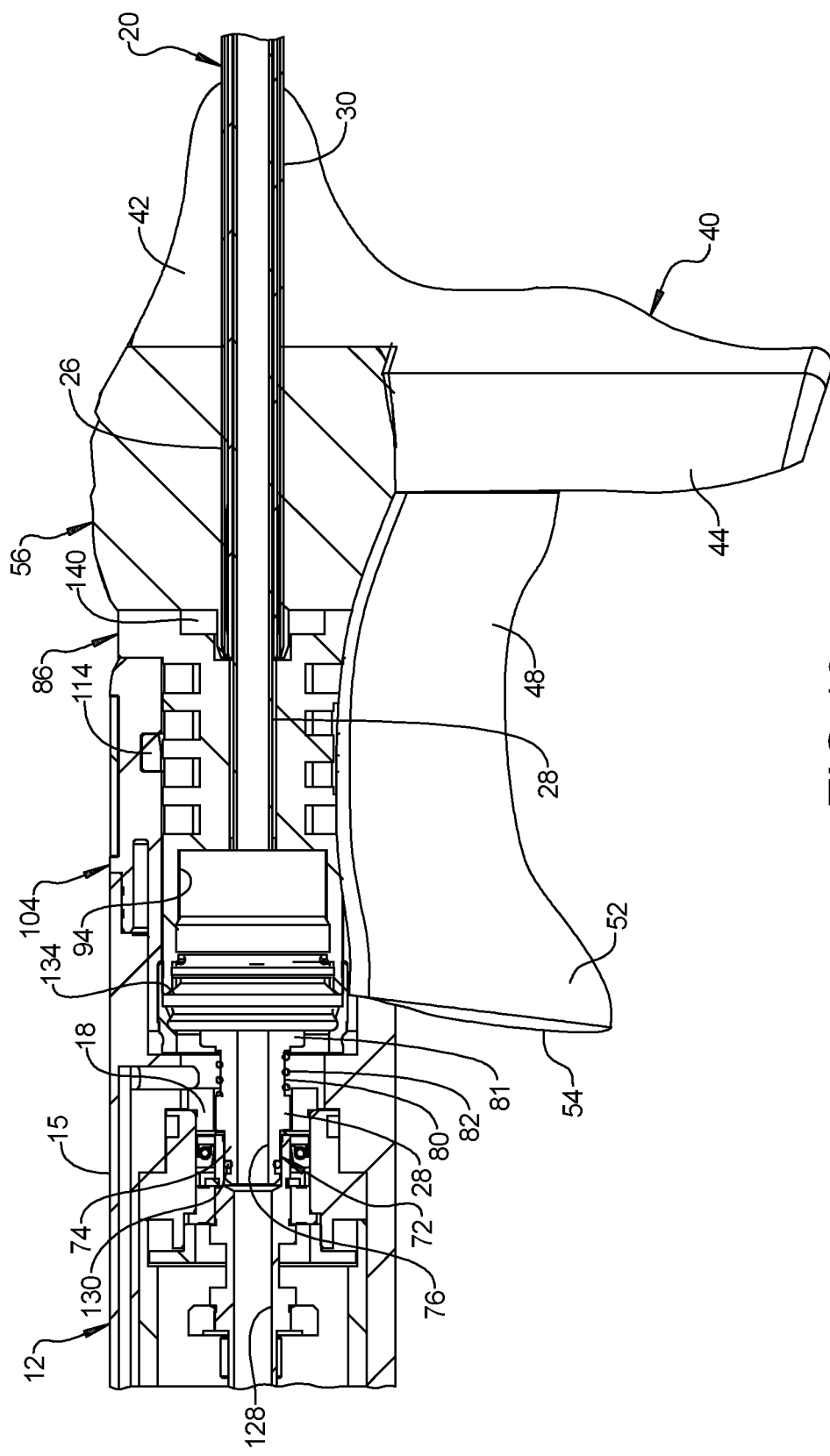
FIG. 19 is an enlarged view of a portion of FIG. 18.
Figure 24:
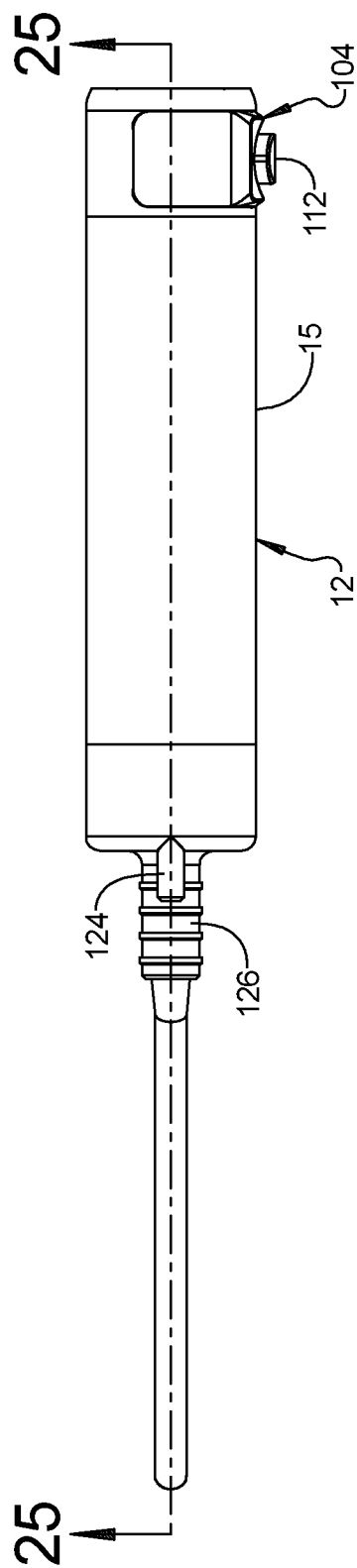
FIG. 24 is a top plan view of the drive assembly of FIG. 22.
Figure 25:
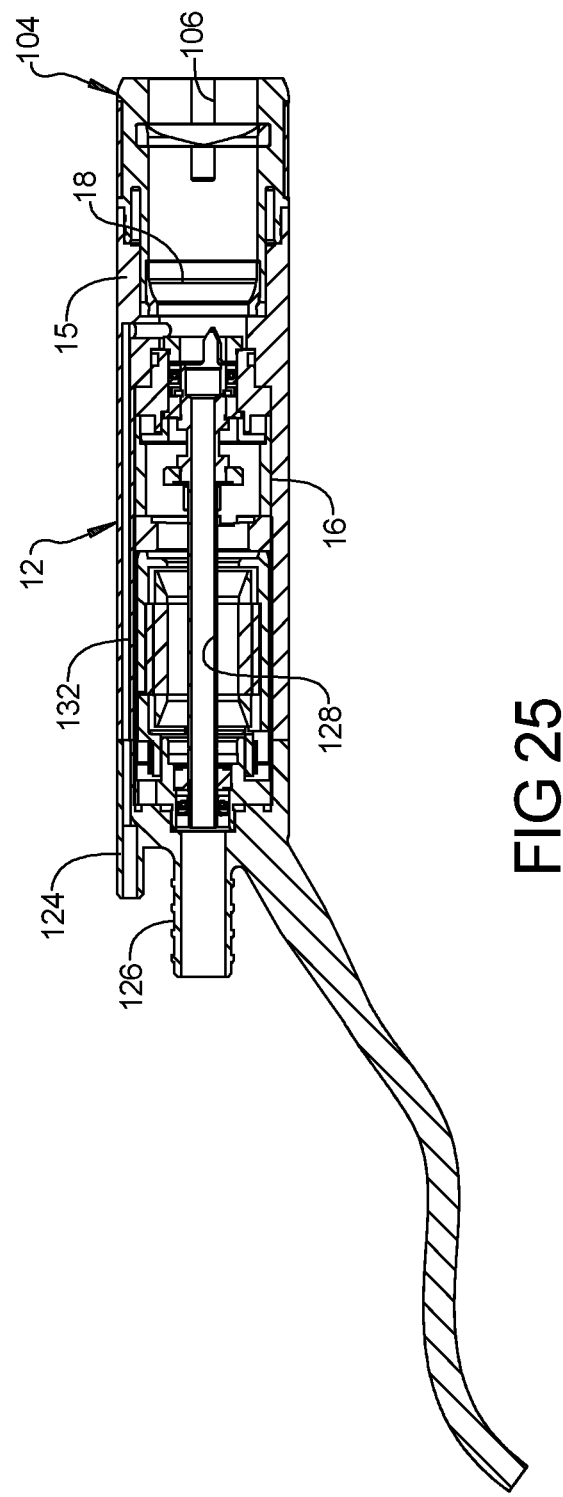
FIG. 25 is a sectional view taken along line 25-25 of FIG. 24.

As illustrated in FIG. 1, the drive assembly 12 includes a housing 15 extending axially. The housing 15 is generally cylindrical in shape. The drive assembly 12 also includes a motor 16 disposed in the housing 15 and having a rotatable drive element 18 (FIG. 17) coupled to the cutting assembly 14. The motor 16 may be of an electric or pneumatic type. In one embodiment, the drive element 18 is removably coupled to the cutting assembly 14 as illustrated in FIG. 16.

It should be appreciated that, in one embodiment, the cutting assembly 14 may be free of any motor. Thus, the cutting assembly 14 may be configured to be disposable after a single-use, or series of uses. It should also be appreciated that, because the cutting assembly 14 may not include any motors, the cost of the cutting assembly 14 may be reduced.

Referring to FIGS. 1-9, the cutting assembly 14 includes a plurality of tubes or tube assembly, generally indicated at 20, extending axially with a window 22, for example, a cutting window, at a distal end 23 adapted to be applied to a surgical site of a patient. The tube assembly 20 has a longitudinal axis 24 defined between the distal end 23 and a proximal end. In one embodiment, the tube assembly 20 includes a first, or outer, tube 26 and a second, or inner, tube 28. The inner tube 28 is removably coupled to and adapted to be rotated by the drive assembly 12, such as by the drive element 18. Rotation of the inner tube 28 by the drive element 18 is relative to the outer tube 26.

Figure 12:
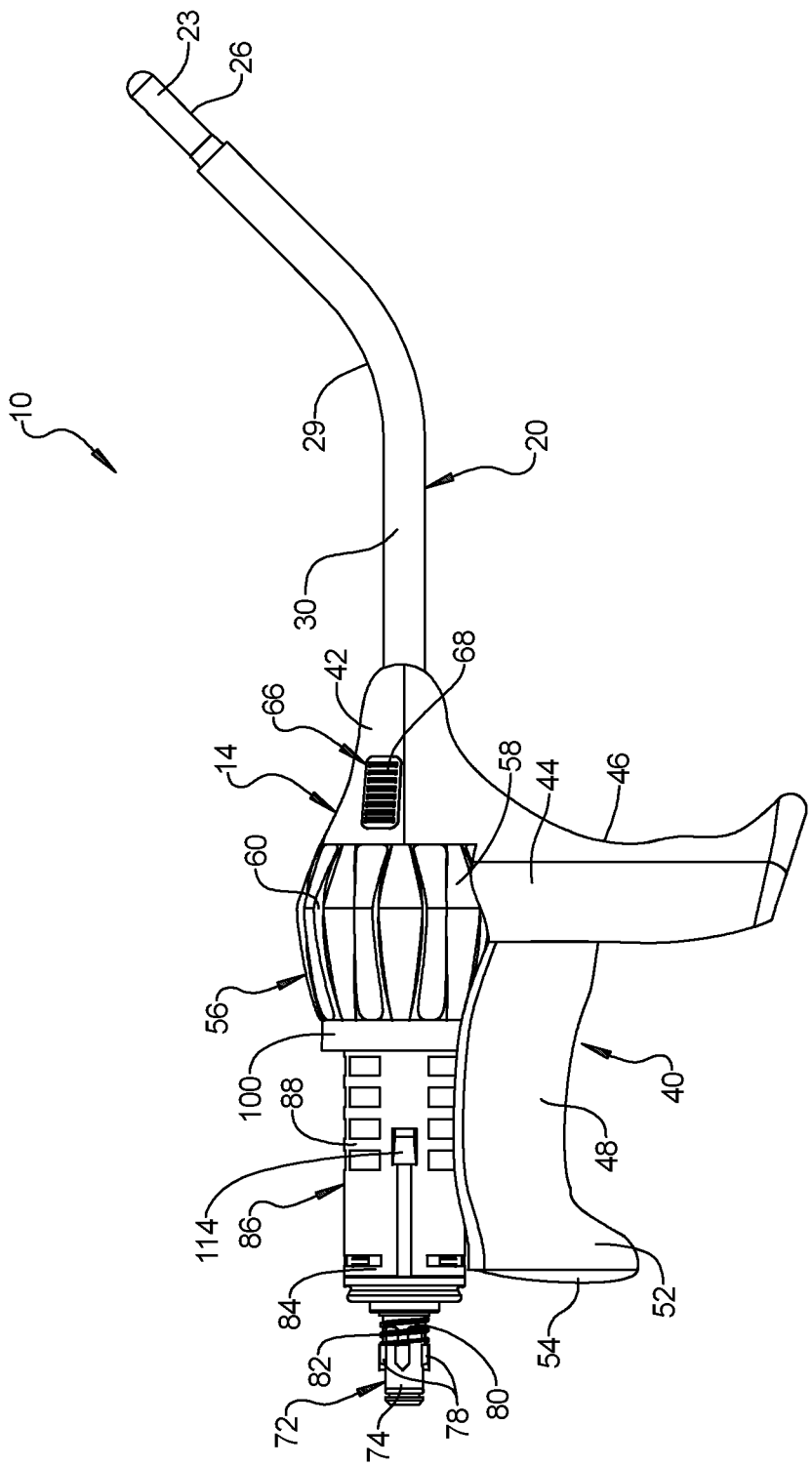
FIG. 12 is an elevational view of a surgical instrument according to another exemplary embodiment of the present disclosure with a drive assembly removed.

Each of the inner tube 28 and the outer tube 26 are generally hollow cylinders and have a generally circular cross-sectional shape. The outer tube 26 has a diameter greater than a diameter of the inner tube 28 such that the inner tube 28 is disposed within the outer tube 26. In other words, the outer tube 26 is disposed over the inner tube 28. The inner tube 28 and the outer tube 26 extend axially between a proximal end and a distal end. In one embodiment, the inner tube 28 may have an axial length longer than an axial length of the outer tube 26 such that the inner tube 28 extends past a proximal end of the outer tube 26 when the inner tube 28 is disposed within the outer tube 26. In another embodiment, the outer tube 26 may have a bend 29 near the distal end 23 thereof as illustrated in FIG. 12. The bend 29 is disposed between the distal end 23 and the proximal end of the outer tube 26.

In one embodiment, the tube assembly 20 may further include a non-rotatable sheath or covering tube 30 disposed about a portion of the outer tube 26. The covering tube 30 has an axial length less than an axial length of the outer tube 26. The covering tube 30 may be angled, straight, or malleable. It should be appreciated that the covering tube 30 is optional. In addition, it should be appreciated that the covering tube 30 may be coupled to the grip 40 such that the covering tube 30 is stationary relative to the grip 40. Furthermore, it should be appreciated that any suitable tubing configuration may be utilized so long as the cutting assembly 14 defines a window and can be driven by the drive assembly 12.

The inner tube 28 and/or outer tube 26 are made of a metal material such as stainless steel or a non-metallic material such as a composite depending on the application. The covering tube 30 may be made of a metal material or a non-metallic material such as a composite depending on the application. It should be appreciated that the wall thickness of the inner tube 28 and the outer tube 26 is relatively thin such as approximately 0.1 to approximately 0.5 millimeters (mm) to allow the tube assembly 20 to be of a relatively small diameter and also to be light-weight. It should also be appreciated that the diameters of the inner tube 28 and the outer tube 26 have a relatively small diameter such as approximately 2.0 mm to approximately 5.0 mm so as to work in a small opening of a nasal cavity or oral cavity of the patient and to prevent the user's view from being obstructed. It should further be appreciated that the inner tube 28 and the outer tube 26 may be scaled larger or smaller depending on the application.

Figure 8:
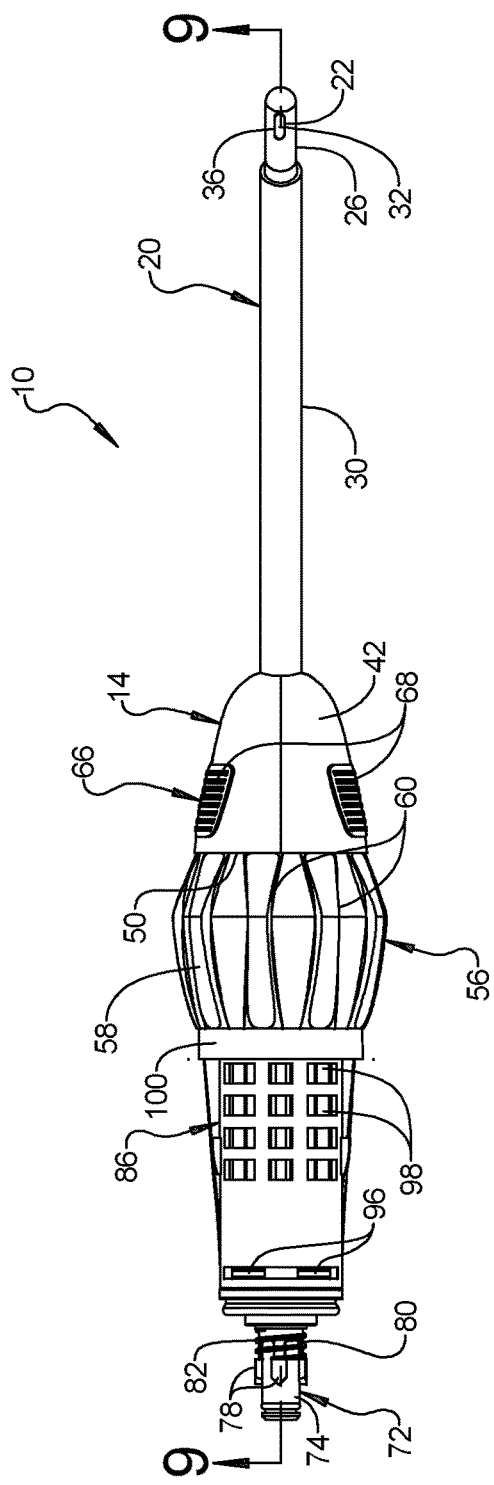
FIG. 8 is a top plan view of the surgical instrument of FIG. 2.
Figure 9:
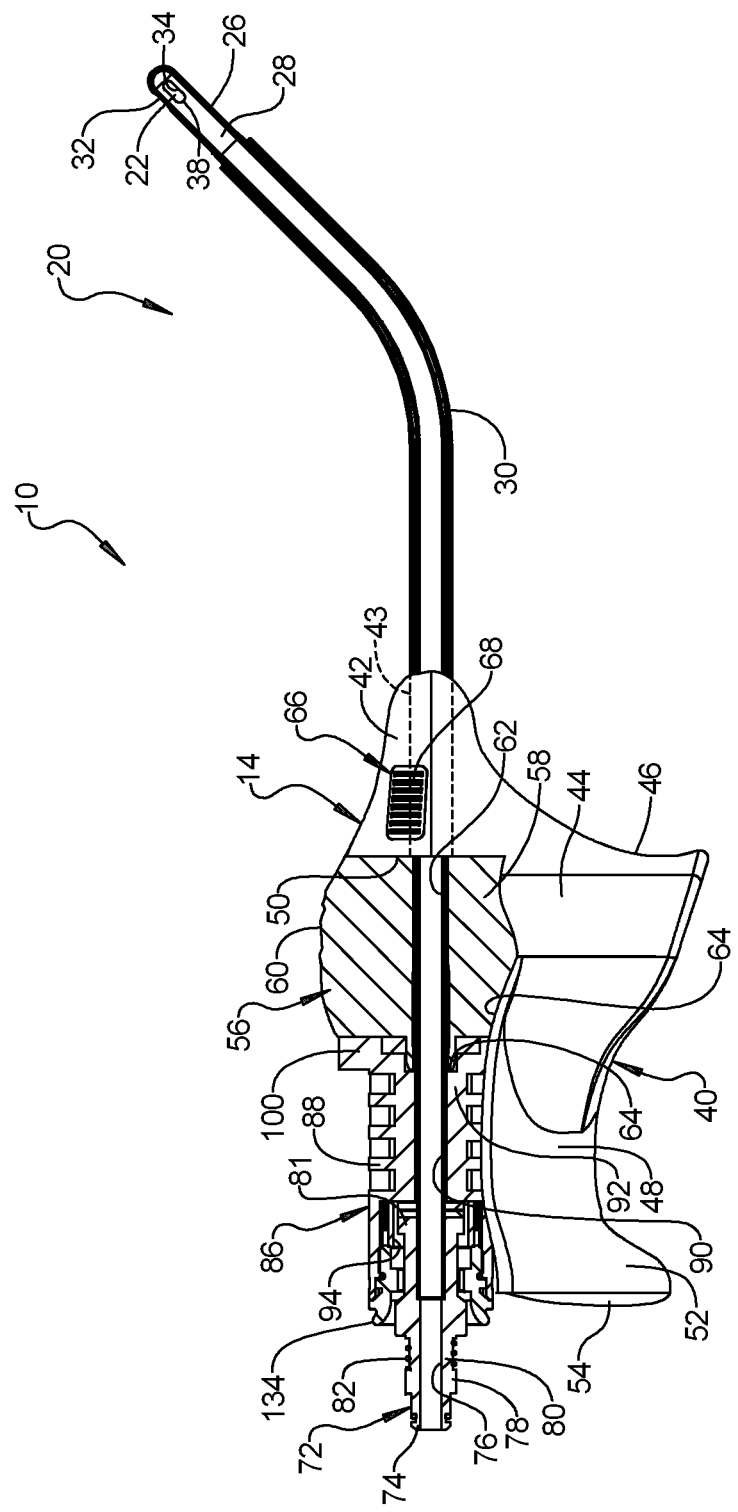
FIG. 9 is a sectional view taken along line 9-9 of FIG. 8.
Figure 34:
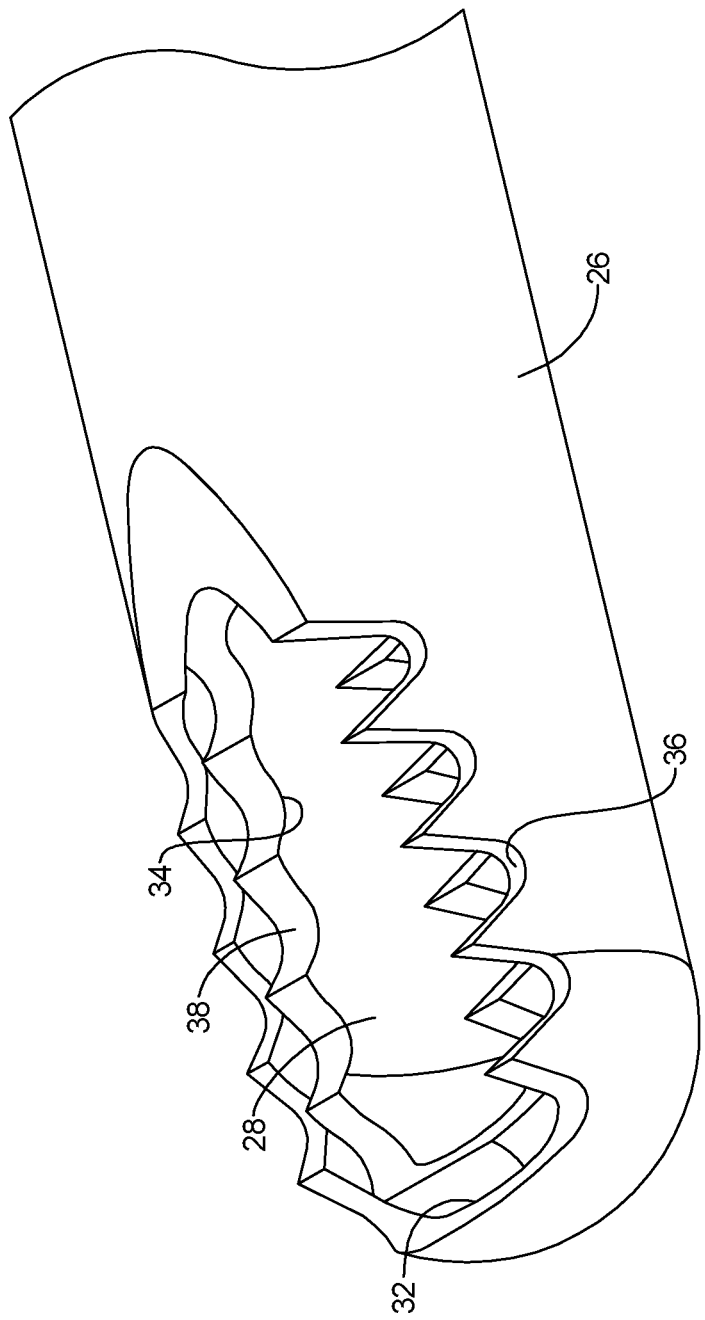
FIG. 34 is a perspective view of a cutting window of the surgical instrument.

As illustrated in FIGS. 8, 9, and 34, the outer tube 26 includes an outer opening or outer aperture 32, and the inner tube 28 includes an inner opening or inner aperture 34. The outer aperture 32 and the inner aperture 34 are generally positioned at or slightly proximal to the distal end 23 of the tube assembly 20. The outer aperture 32 and the inner aperture 34 define the cutting window 22 such that the window 22 extends diametrically through a wall on one side of the tube assembly 20 near the distal end 23 thereof. The openings 32 and 34 are generally elongated in shape, but may be any suitable shape. The outer opening 32 may include at least one serrated edge, knife edge, or resector edge 36. The inner opening 34 is axially aligned with the outer opening 32 and configured to rotate about the longitudinal axis 24 as the drive assembly rotates the inner tube 28. The inner opening 34 may include at least one serrated edge, knife edge, or resector edge 38. It should be appreciated that the serrated edges 36 and 38 allow cutting for the window 22.

The cutting assembly 14 also includes a grip, generally indicated at 40, adapted to be engaged by a least a portion of a hand of a user. As is well understood, and with reference to FIG. 14, the hand H of a user comprises a thumb TH, an index finger IF, secondary fingers SF, a palm P, and a web disposed between the thumb TH and the index finger IF. The secondary fingers SF are the middle, ring, and little fingers of the hand H. The web W may be characterized generally as the lateral surface and a relatively small portion of the palmar surface of the hand H between the thumb TH and the index finger IF. Alternatively, the web W may be characterized as area between the thumb TH and the index finger IF bounded medially by an imaginary line IL (approximated in FIG. 14) extending proximally from between the index finger IF and middle finger of the hand H. In certain characterizations, the palm P of the hand H may be characterized as the level of the superficial palmar arch as commonly referred to in medical literature and approximated in FIG. 14. The web W is lateral of the superficial palmar arch between the thumb TH and the index finger IF. Regardless of characterization, it is to be understood that the palm P does not include the web W of the hand H, and the web W does not include the palm P of the hand H in certain embodiments.

The grip 40 may also support the tube assembly 20. The grip 40 may include a hub or nose portion 42 having an aperture 43 extending axially therethrough to receive the tube assembly 20. The grip 40 also includes a finger portion 44 extending from the nose portion 42 to support a finger of the hand different from the at least one finger. The finger portion 44 defines a front surface 46 and is sized such that the front surface 46 accommodates at least one finger of the hand of the user. In certain embodiments, the finger portion 44 is adapted to be engaged by the index finger IF and/or the secondary finger SF of the hand. It should be appreciated that, in another embodiment, the nose portion 42 may not be part of the grip 40 and be separate and distinct from the grip 40.

Figure 1A:
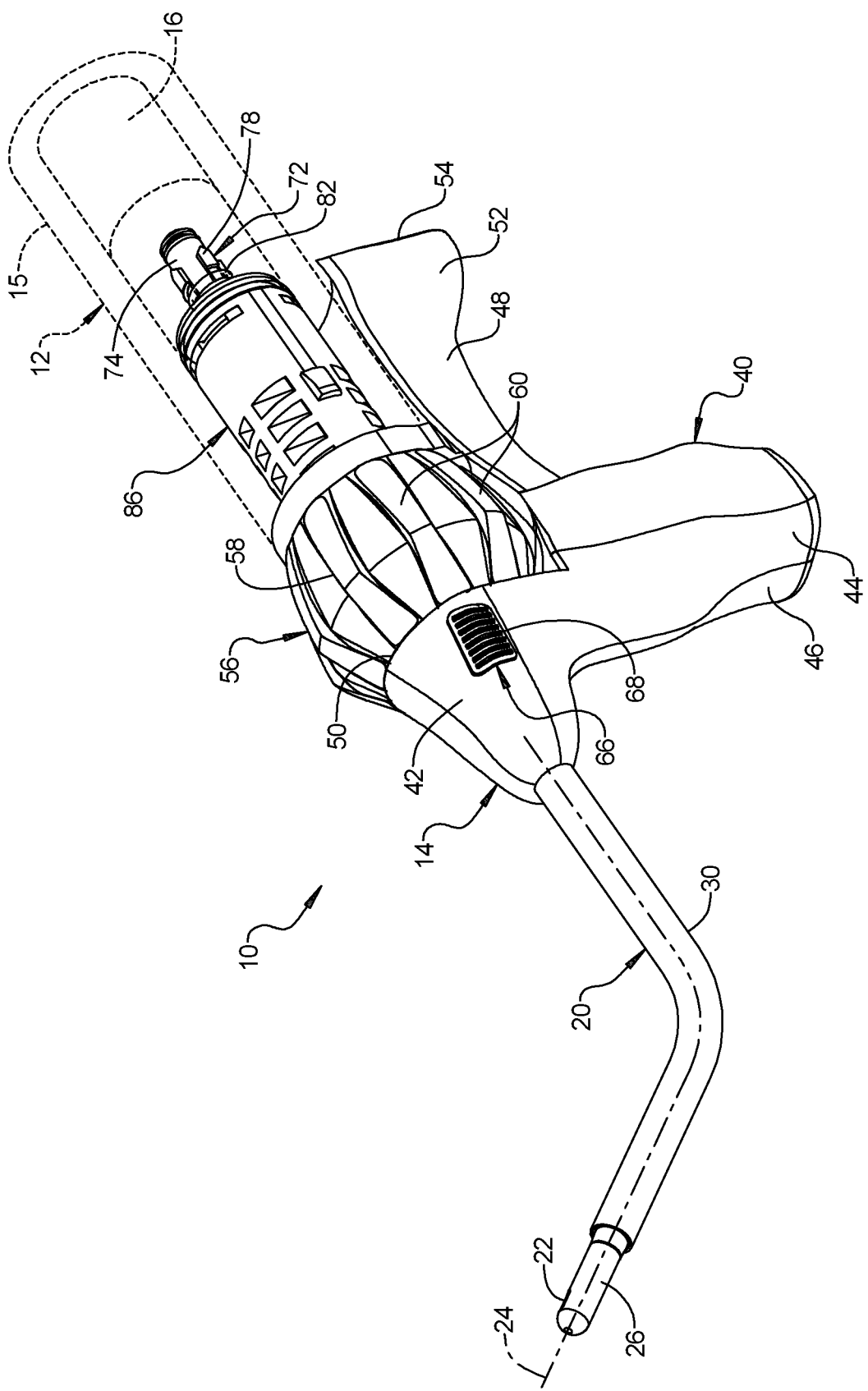
FIG. 1A is a perspective view of a surgical instrument according to another exemplary embodiment of the present disclosure. The drive assembly is shown in phantom.

In certain embodiments, the finger portion 44 extends from the nose portion 42 at an angle between at least perpendicular and an obtuse angle relative to the nose portion 42. Thus, in those embodiments, it should be appreciated that the angle between the finger portion 44 and the nose portion 42 does not form an acute angle. It should also be appreciated that, in the embodiment illustrated in FIG. 1A, the finger portion 44 is longer than the finger portion 44 of the embodiment of FIG. 1.

As used therein, the term "grip" is a portion that can be used for any type of cutting instrument such as burs, shavers, or any other device imaginable that couples to a handpiece including a motor. It should be appreciated that the term "grip" may provide for both pencil and pistol types. It should also be appreciated that the grip 40 may be a hybrid between a pencil grip and a pistol grip and combines the advantages of both by providing the hand-held like pencil and the web-like pistol features of the pencil grip and the pistol grip, respectively.

Figure 2:
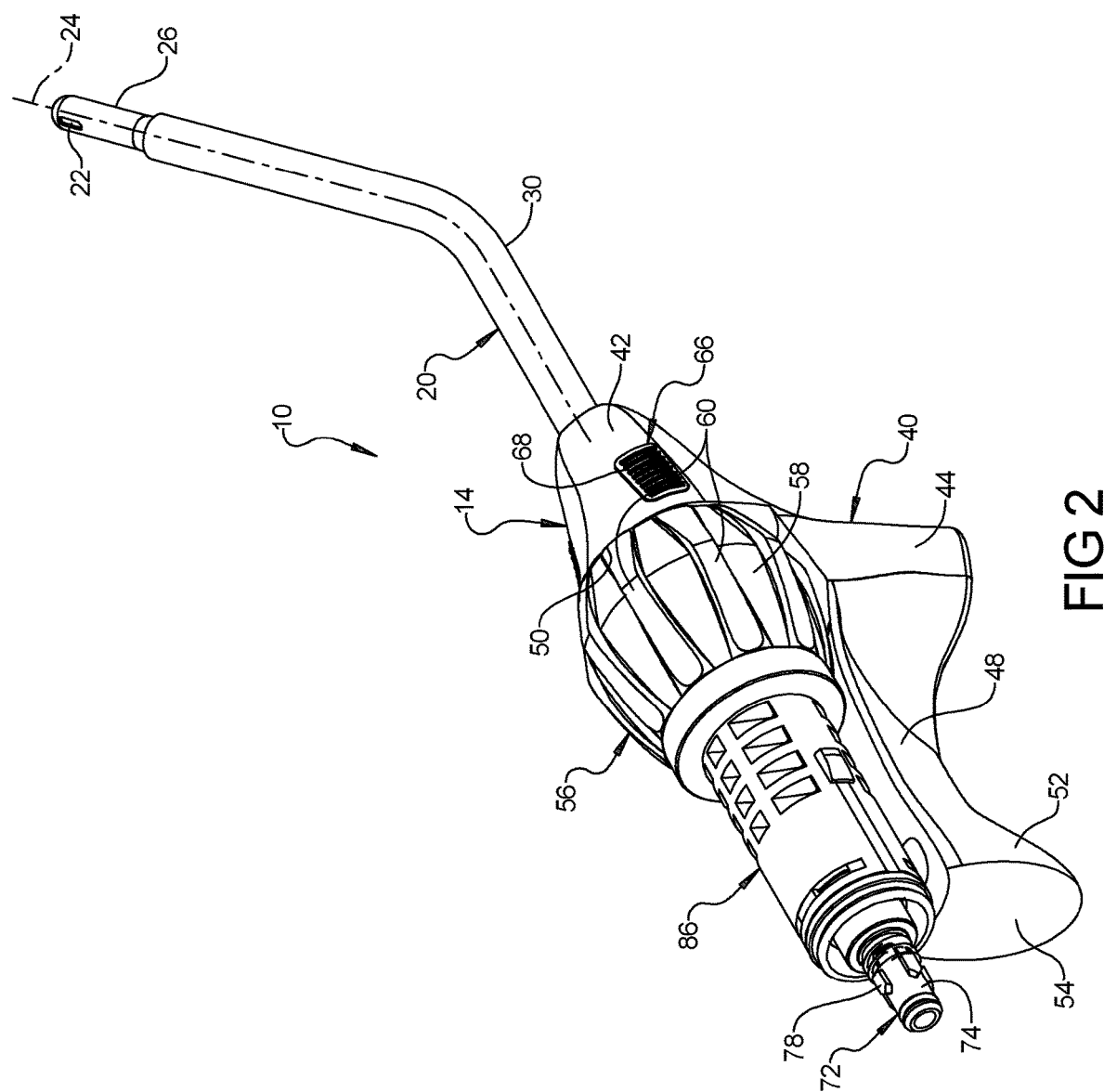
FIG. 2 is a perspective view of the surgical instrument of FIG. 1 with a drive assembly removed.
Figure 3:
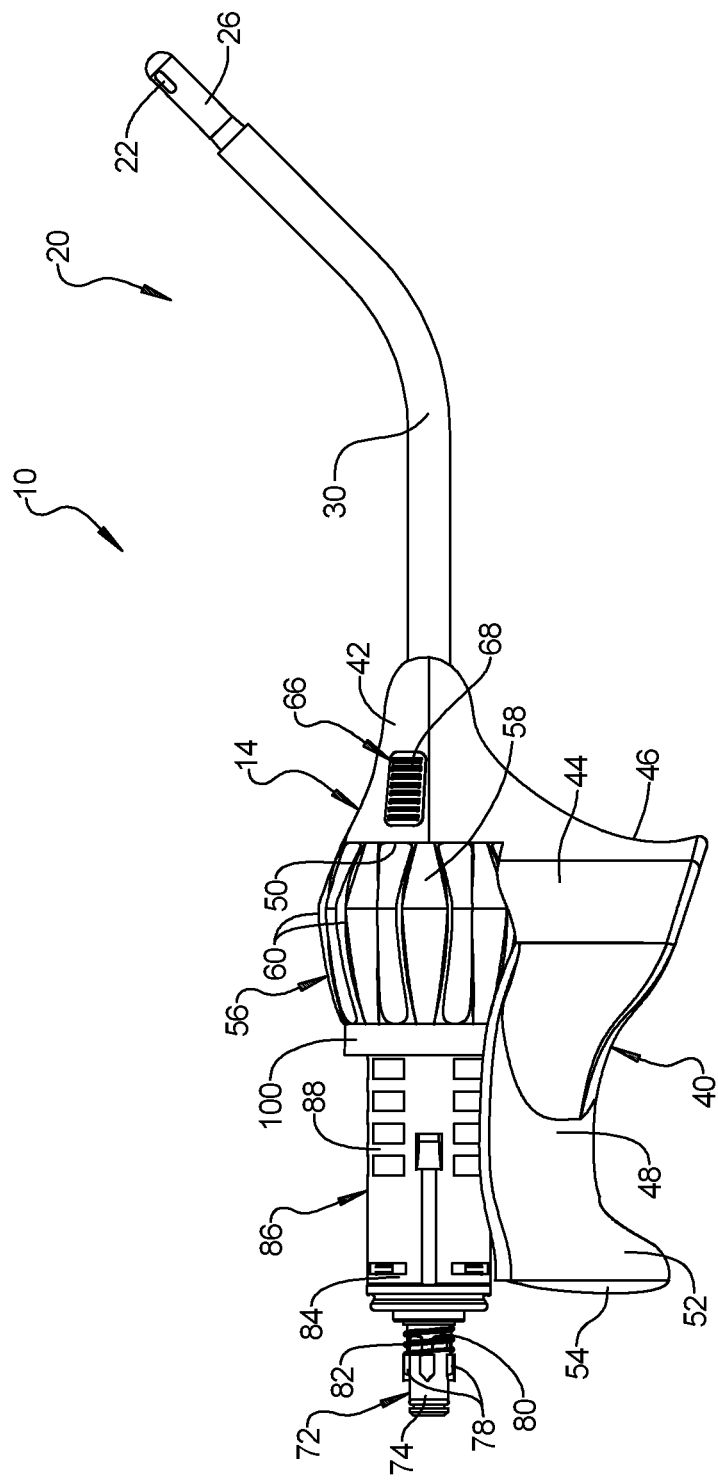
FIG. 3 is a right side elevational view of the surgical instrument of FIGS. 1 and 2 with the drive assembly removed.
Figure 4:
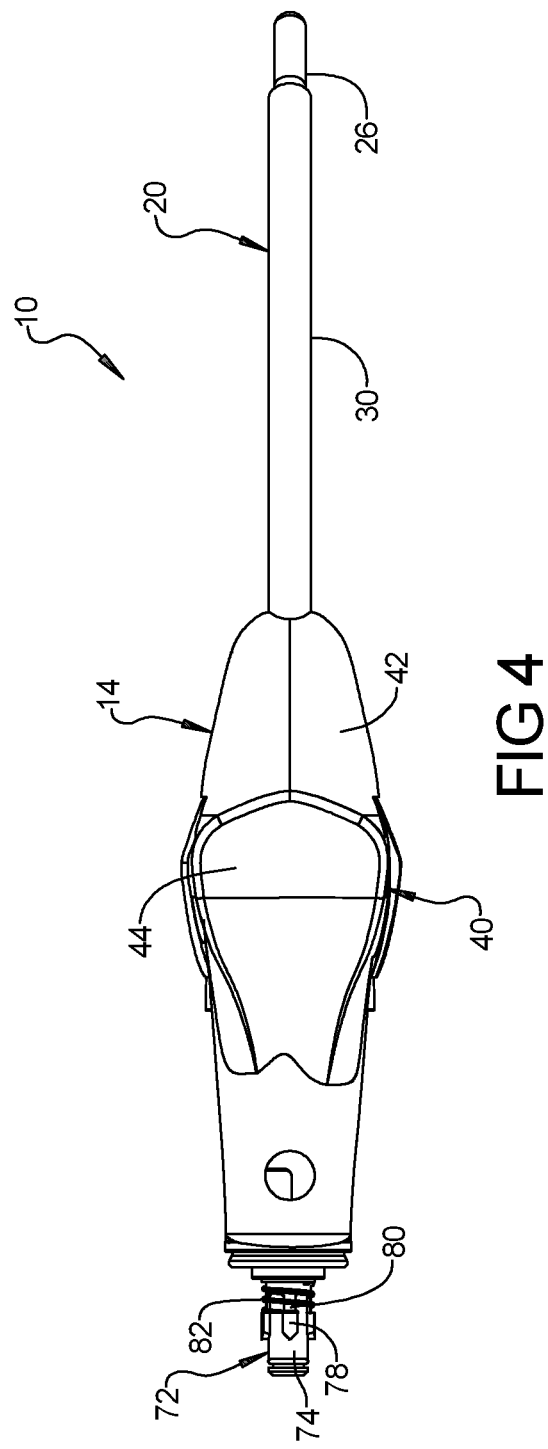
FIG. 4 is a bottom plan view of the surgical instrument of FIG. 2.

In certain embodiments illustrated in FIGS. 1-9, the grip 40 may include an intermediate portion 48 extending axially from the finger portion 44 towards the drive assembly 12. As illustrated in FIGS. 2 and 3, the intermediate portion 48 forms an open area ledge 50 with the nose portion 42. The open area ledge 50 may be contoured relative to a manually movable member, generally indicated at 56, and a connecting hub, generally indicated at 86, to be described. It should be appreciated that the dimensions of the intermediate portion 48 are not particularly limited, and may be customized to suit the dimensions of a user's hand. It should also be appreciated that the intermediate portion 48 is optional and a web portion 52 to be described may be directly coupled to the housing 15 of the drive assembly 12.

Figure 5:
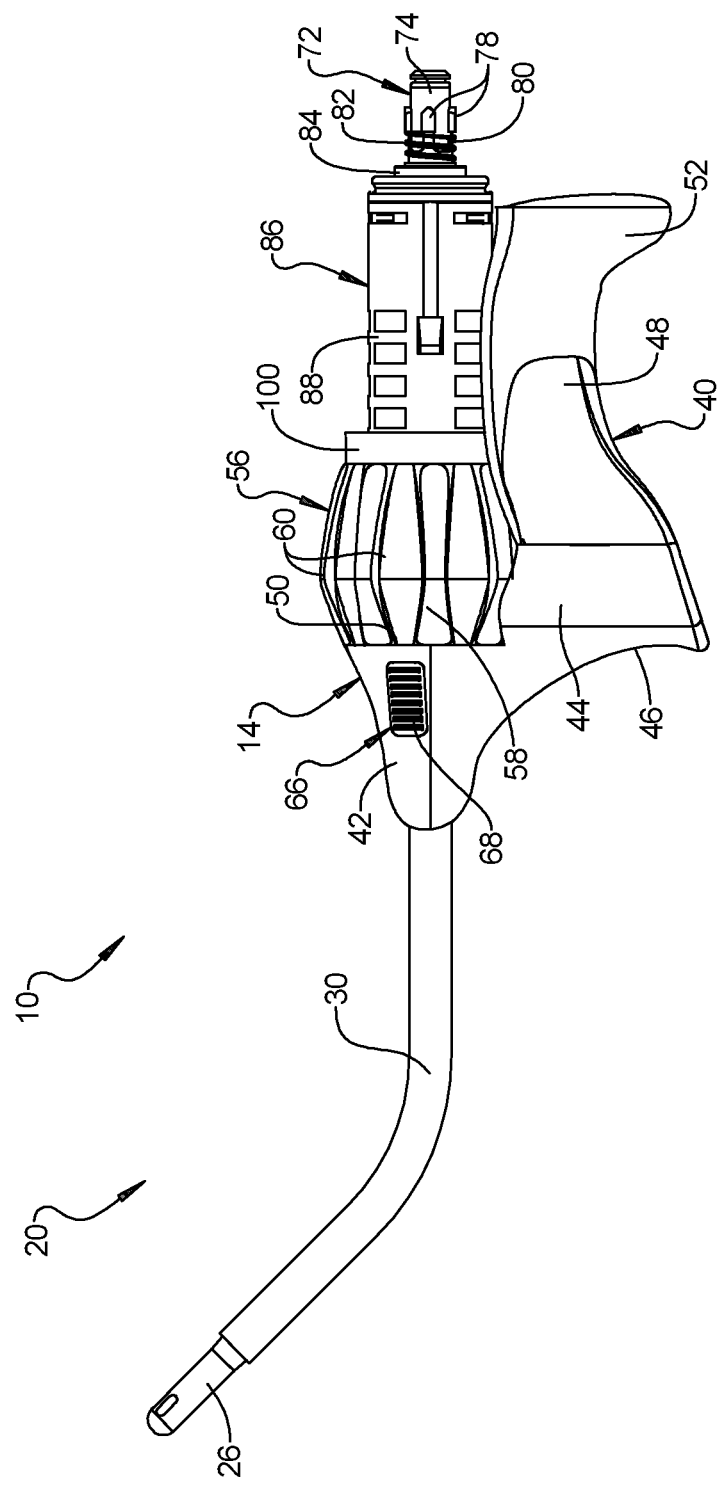
FIG. 5 is a left side elevational view of the surgical instrument of FIG. 2.
Figure 6:
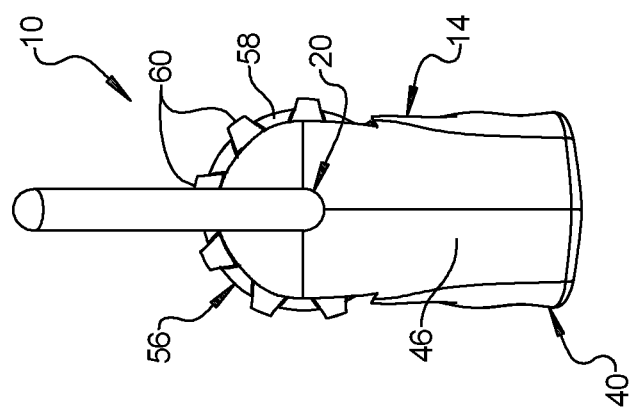
FIG. 6 is an elevational view the surgical instrument of FIG. 2 viewed from the proximal end.
Figure 7:
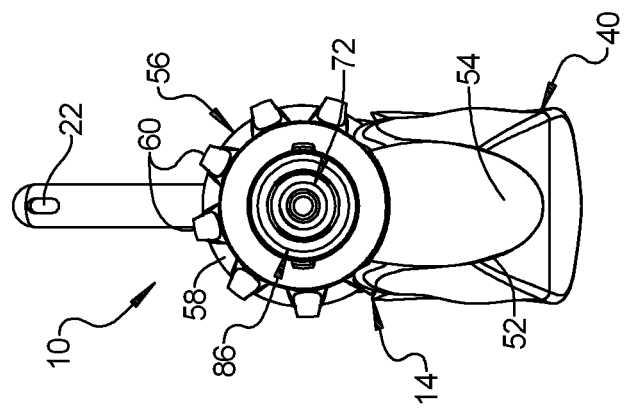
FIG. 7 is an elevational view of the surgical instrument of FIG. 2 viewed from the distal end.
Figure 13:
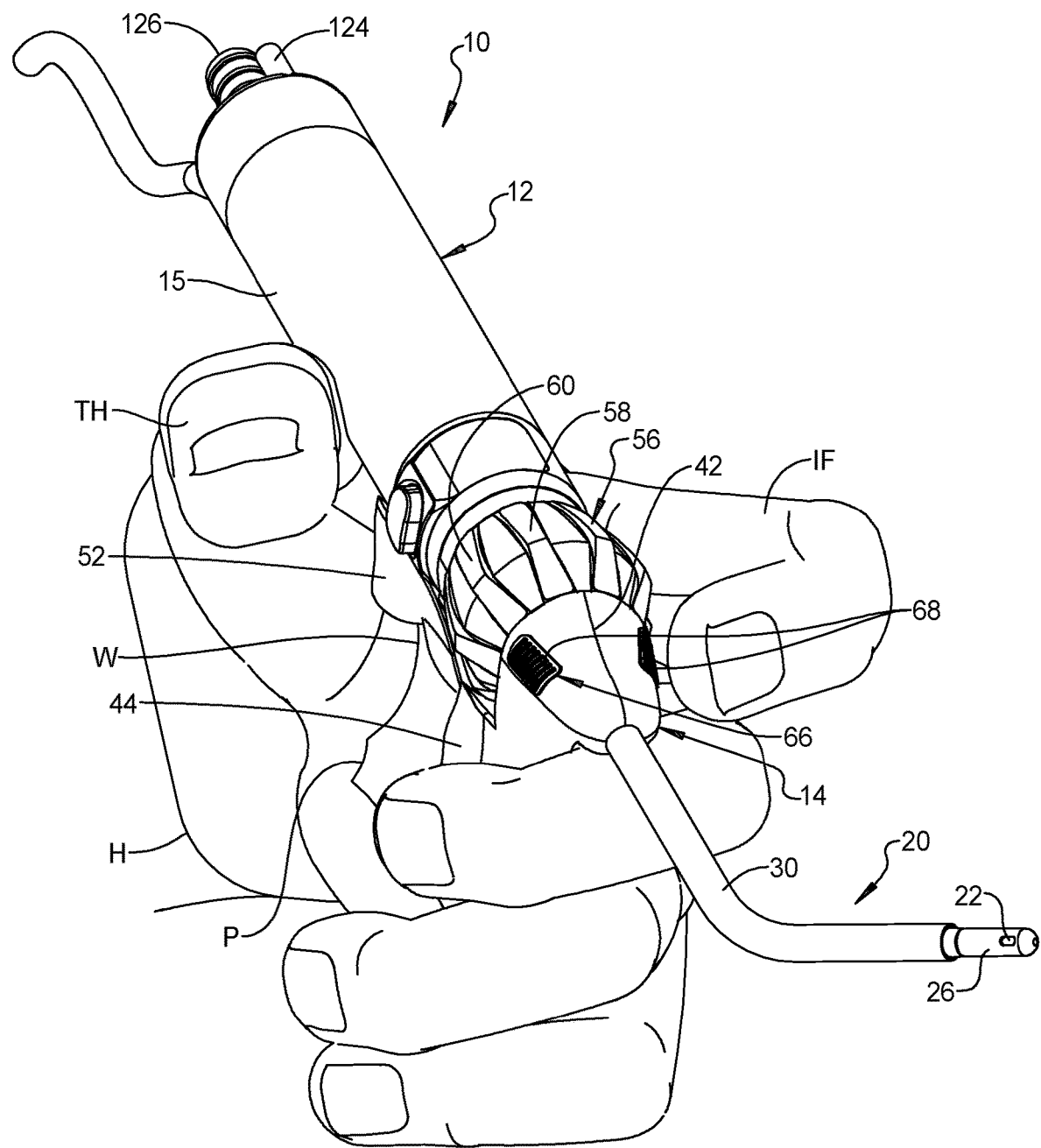
FIG. 13 is a perspective view of the surgical instrument of FIG. 1A illustrated in operational relationship with a hand of a user.

The grip 40 also includes the web portion 52. In FIG. 5, the web portion 52 extends from the intermediate portion 48 and apart from the finger portion 44 to engage the web W of the hand H as illustrated in FIG. 13. The web portion 52 is adapted to be engaged by the web W of the hand H without being engaged by the palm P of the hand H. The web portion 52 has a rear surface 54 to engage the web W of the hand.

It should be appreciated that, in certain embodiments, the rear surface 54 may be substantially parallel to the front surface 46. It should also be appreciated that the front surface 46 may be substantially perpendicular to a proximal portion of the tube assembly 20.

In one embodiment, the nose portion 42, finger portion 44, intermediate portion 48, and web portion 52 may be integral, unitary, and formed as one-piece. In certain embodiments, such as those illustrated in FIGS. 1 and 1A, each of the finger portion 44 and the web portion 52 extend away from the intermediate portion 48 in a direction opposite the housing 15 or a moveable member 56 to be described to define a generally U-shaped configuration of the grip 40. It should be appreciated that, in one embodiment, the grip 40 may be separable from the inner tube 28 of the tube assembly 20.

In another embodiment, a position of the web portion 52 is adjustable relative to a position of the finger portion 44. In such an embodiment, the web portion 52 extends downwardly from the intermediate portion 44 of the grip 40. The web portion 52 may be extendable or have a longer length to accommodate various hand sizes of users.

Figure 10:
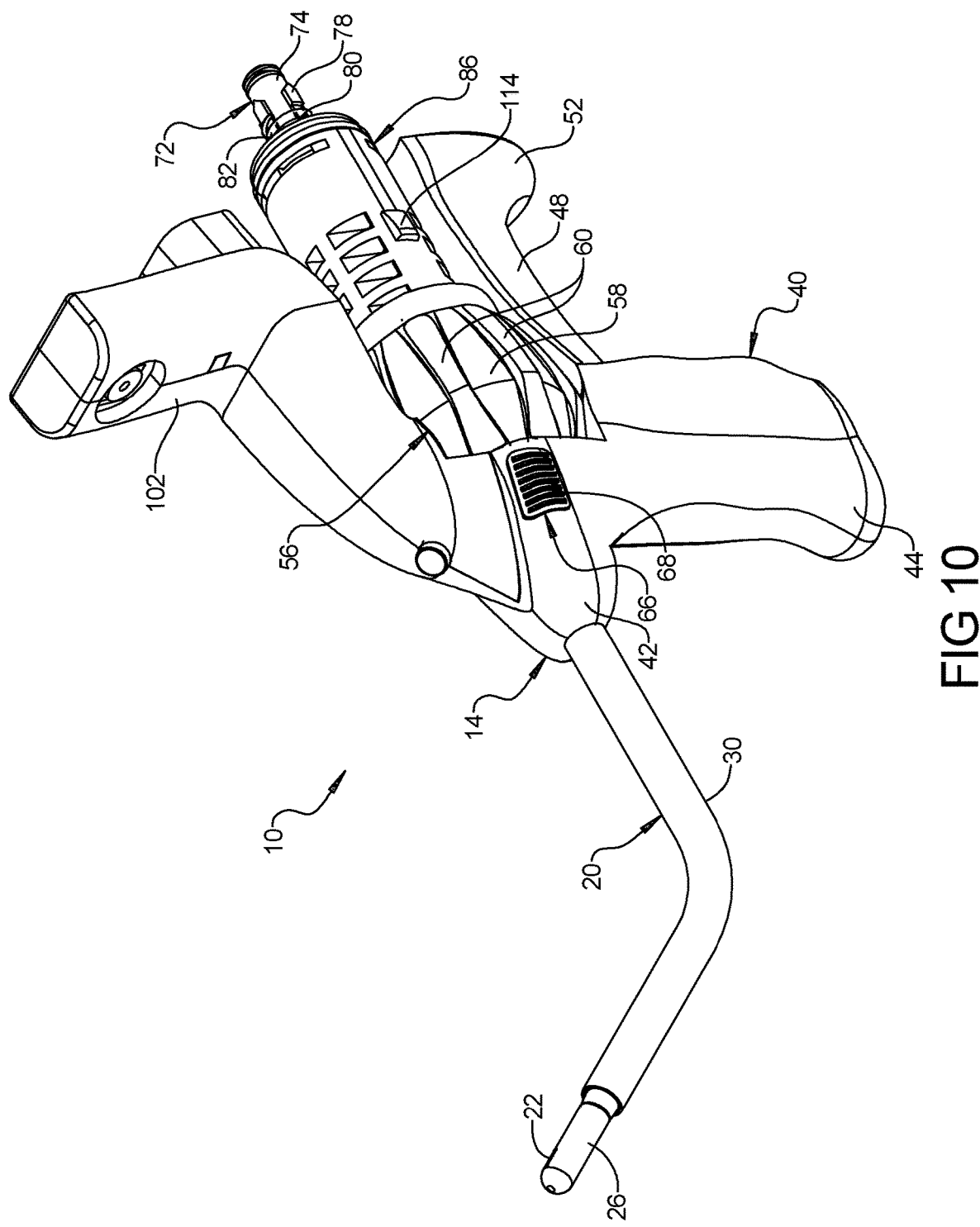
FIG. 10 is a perspective view of a surgical instrument according to another exemplary embodiment of the present disclosure with a drive assembly removed, and a tracking element coupled to a cutting assembly of the surgical instrument.

The web portion 52 and the finger portion 44 each have a length extending away from the tube assembly 20. In one embodiment, the length of the finger portion 44 is greater or larger than the length of the web portion 52 as illustrated in FIG. 10. In other embodiments, the length of the finger portion 44 is substantially the same length as the length of the web portion 52 as illustrated in FIG. 1.

In certain embodiments, the grip 40 may have still other configurations that allow the user to grasp the grip 40 and operate the surgical instrument 10.

Figure 14:
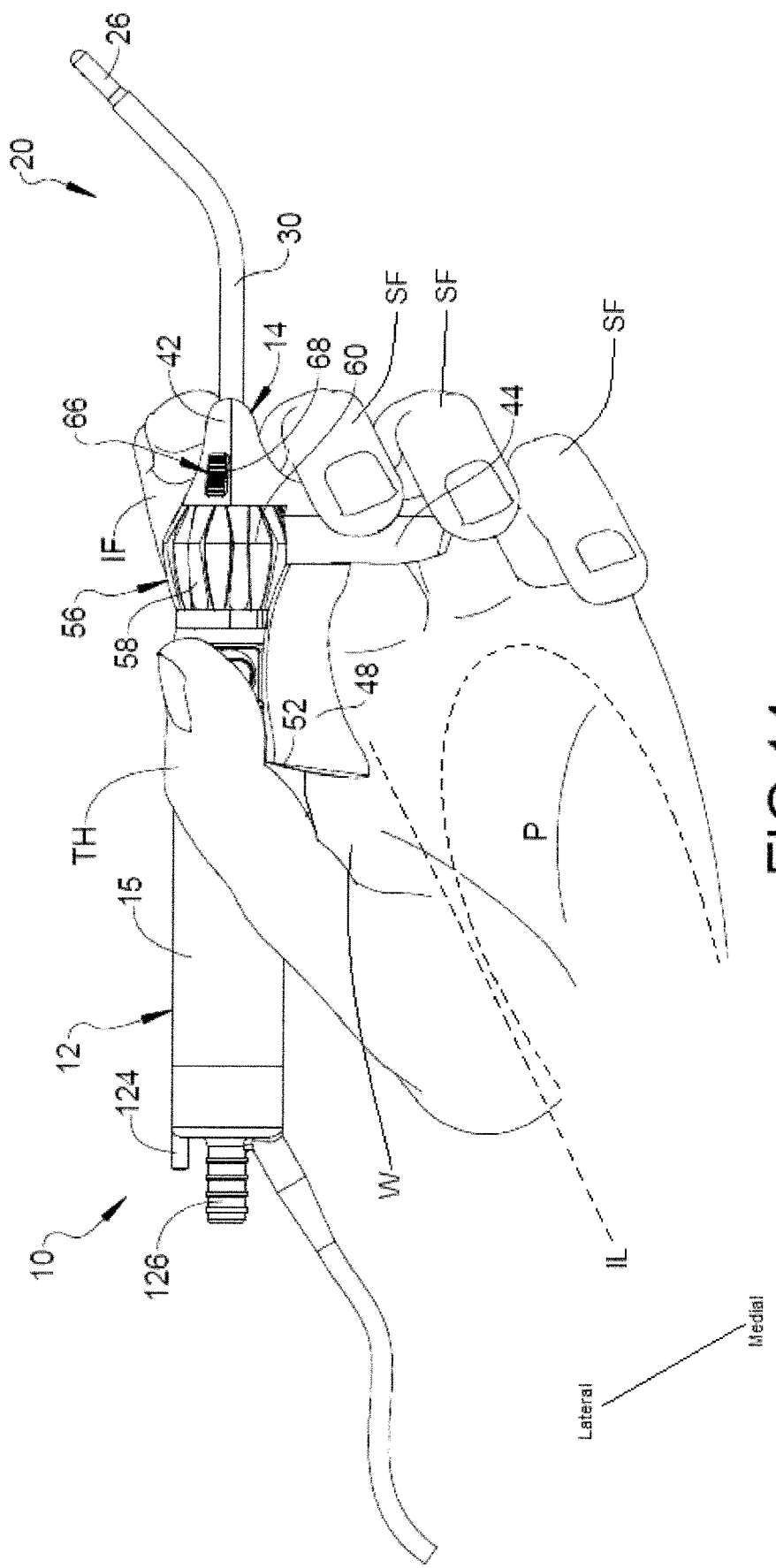
FIG. 14 is an elevational view of the surgical instrument of FIG. 1A illustrated in operational relationship with a hand of a user.

As illustrated in FIGS. 13 and 14, the hand of the user is used to grasp or grip the grip 40. The user places the web W of the hand on the web portion 52 and at least one finger of the hand H on the front surface 46 of the finger portion 44 of the grip 40. When the hand H is engaged with the grip 40, a palm P of the user's hand H does not engage the grip 40 as is done with conventional handles or pistol grips. Rather, in certain embodiments, the index finger IF or the secondary finger SF engaging the finger portion 44, together with the web W of the hand H engaging the web portion 52, provide opposing forces to the grip 40 so as to grasp the grip 40. In effect, the grip 40 is squeezed between the index finger IF or secondary finger SF and the web W of the hand without the palm P of the hand H engaging the grip 40. It should be appreciated that the features that allow the hand H to engage the grip 40 in the manner described above are based on the design of the grip 40.

Referring to FIGS. 1-14, the cutting assembly 14 further includes a manually movable member, generally indicated at 56, coupled to the tube assembly 20 and located axially along the grip 40. More particularly, the manually movable member 56 is coupled to the outer tube 26 and adapted to be rotated by the user to rotate the outer tube aperture about the longitudinal axis 24. The manually movable member 56 is positioned to be within reach of the thumb TH or at least one finger of the hand H of the user when the web W of the hand H is engaged with the grip 40 to allow the thumb TH or the at least one finger, such as the index finger IF, to rotate the window 22 of the tube assembly 20 relative to the longitudinal axis 24 of the tube assembly 20. In certain embodiments, the manually movable member 56 is adapted to be rotated with both the index finger IF and the thumb B of the hand H while the finger portion 44 is engaged by the secondary finger SF of the hand and the web portion 52 is engaged by the web W of the hand. In one embodiment, the manually movable member 56 is located axially along the grip 40 and within at least twenty, thirty, forty, fifty, sixty, or seventy percent of an axial length from the distal end of the nose portion 42. This positioning allows the user's thumb TH or index finger IF to actuate the manually movable member 56 while the web W of the user's hand H engages the web portion 52 of the grip 40. It should be appreciated that the manually movable member 56 is part of the cutting assembly 14 and not part of the drive assembly 12.

In the illustrated embodiment, the manually movable member 56 includes a rotatable wheel 58 coupled to the outer tube 26 to allow the at least one finger of the hand H of the user to rotate the outer tube 26 relative to the longitudinal axis 24. The rotatable wheel 58 is generally circular in shape, but may be any suitable shape. The rotatable wheel 58 includes a plurality of gripping members 60 extending radially and axially and spaced circumferentially to allow the user to rotate the rotatable wheel 58. The rotatable wheel 58 also includes an aperture 62 extending axially therethrough to allow the rotatable wheel 58 to be disposed over and about the outer tube 26 as illustrated in FIG. 9. The rotatable wheel 58 further includes a projection 70 extending axially. The rotatable wheel 58 is made of a non-metallic material. The rotatable wheel 58 is integral, unitary, and formed as one-piece. It should be appreciated that the rotatable wheel 58 is coupled to the outer tube 26 through a suitable mechanism, for example a knurled area of the aperture 68, to form a friction fit, adhesive bond, or induction bond.

Figure 26A:
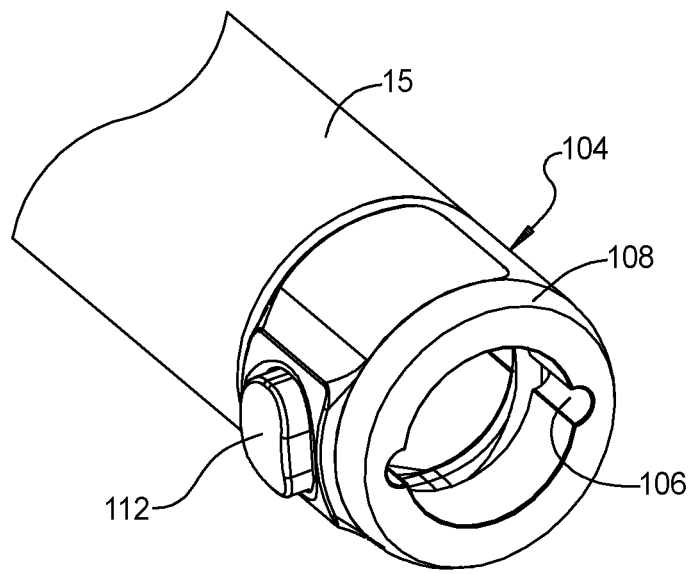
FIG. 26A is a fragmentary perspective view of the drive assembly.
Figure 26B:
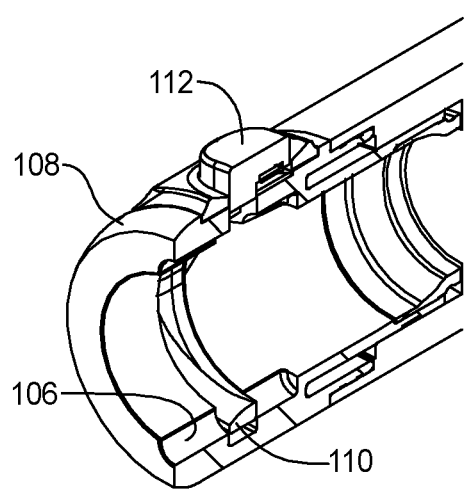
FIG. 26B is a fragmentary perspective view of the portion of the drive assembly of FIG. 26A.
Figure 27:
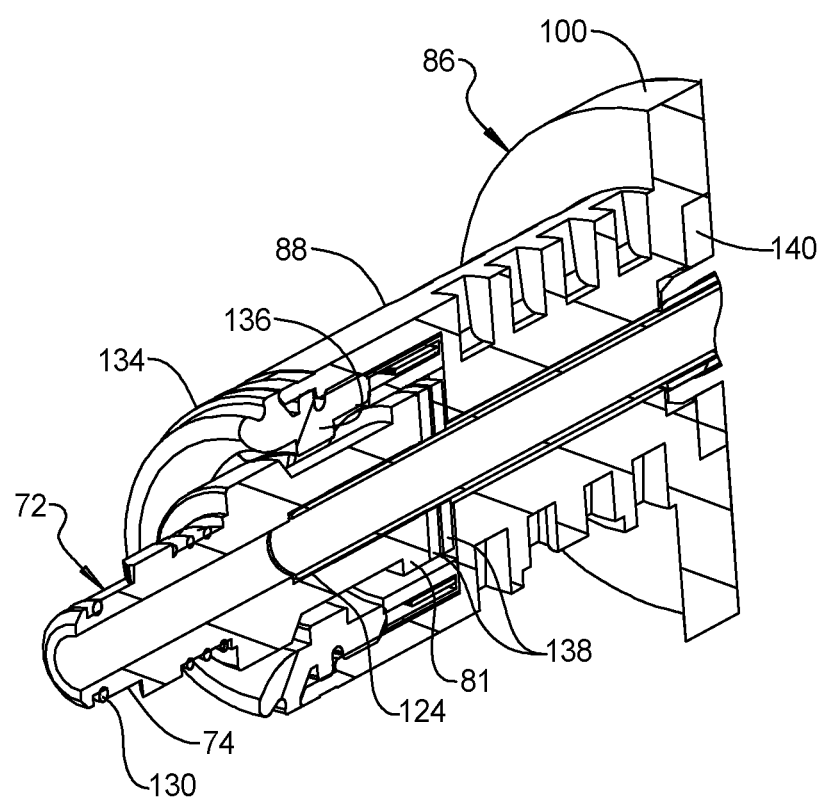
FIG. 27 is a fragmentary sectional perspective view of the cutting assembly.
Figure 28A:
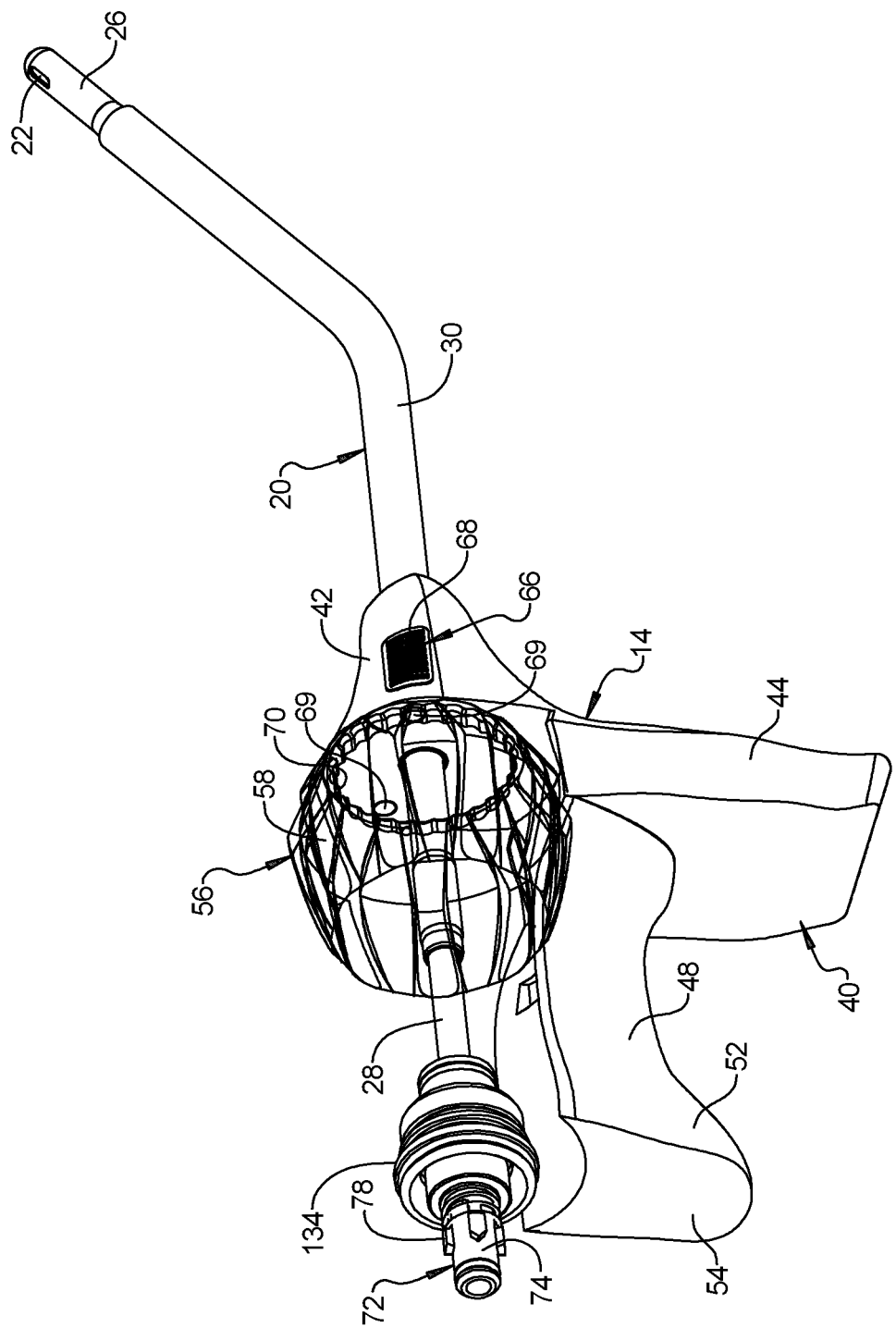
FIG. 28A is a perspective view of the cutting assembly.
Figure 28B:
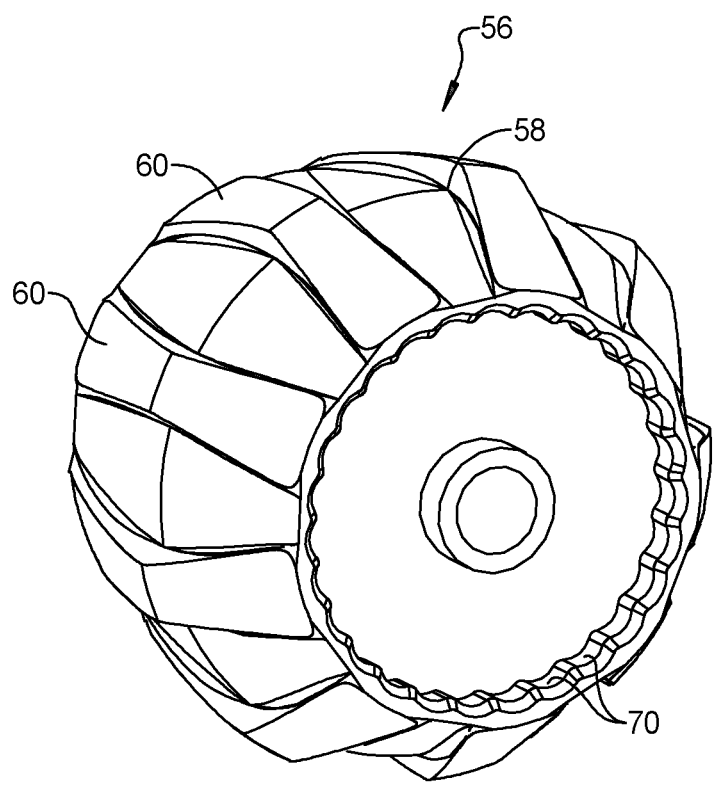
FIG. 28B is a perspective view of a manually movable member of the cutting assembly of FIG. 26.

Referring to FIGS. 13, 14, and 26, the manually movable member 56 may include a locking assembly, generally indicated at 66, cooperating with the grip 40 to lock the rotatable wheel 58 in place relative to the nose portion 42 of the grip 40. The locking assembly 66 includes one or more movable locking members 68 having a pin 69 at one axial end to be disposed in one or more recesses 70 spaced circumferentially about the rotatable wheel 58 as illustrated in FIG. 26. In one embodiment, two movable locking members 68 are disposed on opposed sides of the nose portion 42 to allow a right-handed or left-handed user to operate one of the movable locking members 68. More particularly, the movable locking members 68 are adapted to be engaged by the index finger IF or the thumb TH of the hand H while the grip 40 is engaged by the web W of the hand H. Thus, the user may lock the manually movable member 68 from rotating relative to the grip 40 without needing to use a secondary hand or significantly readjust one's grip on the cutting assembly 14. It should be appreciated that the user slides the movable member 68 distally to disengage the pin 69 from one of the recesses 70, rotates the rotatable wheel 58, and slides the movable locking member 68 proximal to engage the pin 69 with another recess 70 to lock the rotatable wheel 58 in place. It should be appreciated that the number of recesses 70 are not particularly limited and may correspond to a number of predetermined positions, etc.

The cutting assembly 14 also includes a drive hub, generally indicated at 72, disposed about a proximal end of the inner tube 28 to allow the inner tube 28 to be connected to the drive element 18 for rotation of the inner tube 28 about the longitudinal axis 24. The drive hub 72 includes a hub member 74 disposed about the inner tube 28. The hub member 74 extends axially and is generally cylindrical in shape. The hub member 74 has an aperture 76 extending axially therethrough to receive the inner tube 28 as illustrated in FIG. 9. The hub member 74 also includes a plurality of projections 78 extending radially and axially and spaced circumferentially thereabout. The hub member 74 further includes a reduced diameter portion 80 adjacent the protections 78. The hub member 74 also includes a flange 81 extending radially at a distal end thereof. The hub member 74 is made of a non-metallic material. The hub member 74 is integral, unitary, and formed as one-piece. The drive hub 72 includes a spring 82 disposed about the hub member 74 in the reduced diameter portion 80. It should be appreciated that the drive hub 72 allows for rotation of the inner tube 28 and may allow for the transfer of fluid through the inner tube 28. It should also be appreciated that a variety of drive coupling configurations may be used with the cutting assembly 14.

The cutting assembly 14 further includes a connecting hub, generally indicated at 86, disposed about the inner tube 28 and a portion of the drive hub 72 to allow the drive assembly 12 to be coupled to the cutting assembly 14. The connecting hub 86 includes a coupling member 88 disposed about the inner tube 28. The coupling member 88 extends axially and is generally cylindrical in shape. The coupling member 88 has an aperture 90 extending axially therethrough to receive the inner tube 28. The coupling member 88 includes a first or distal cavity 92 extending axially therein to receive the projection 70 of the rotatable wheel 58 and a second or proximal cavity 94 extending axially therein to receive a distal end of the fluid coupling 72. The proximal cavity 94 includes at least one raised area 95 extending axially and radially from an axial end thereof to allow fluid flow between a bushing 138 to be described and the connecting hub 86. The coupling member 88 also includes a plurality of recesses 96 extending circumferentially and radially and spaced circumferentially about the coupling member 88. The coupling member 88 includes a plurality of recesses 98 extending radially and circumferentially therein. The coupling member 88 also includes a flange 100 extending radially and disposed axially therealong to act as a stop against the rotatable member 56. The coupling member 88 includes one or more projections 101 extending radially from the flange 100 and spaced circumferentially from each other. The projections 101 are disposed in either corresponding apertures or a groove 101a (FIG. 30) in the intermediate portion 44 of the grip 40 to prevent rotation of the coupling member 88. The coupling member 88 is made of a non-metallic material. The coupling member 88 is integral, unitary, and formed as one-piece. It should be appreciated that the drive coupling 86 allows for the coupling of the drive assembly 12.

Figure 11:
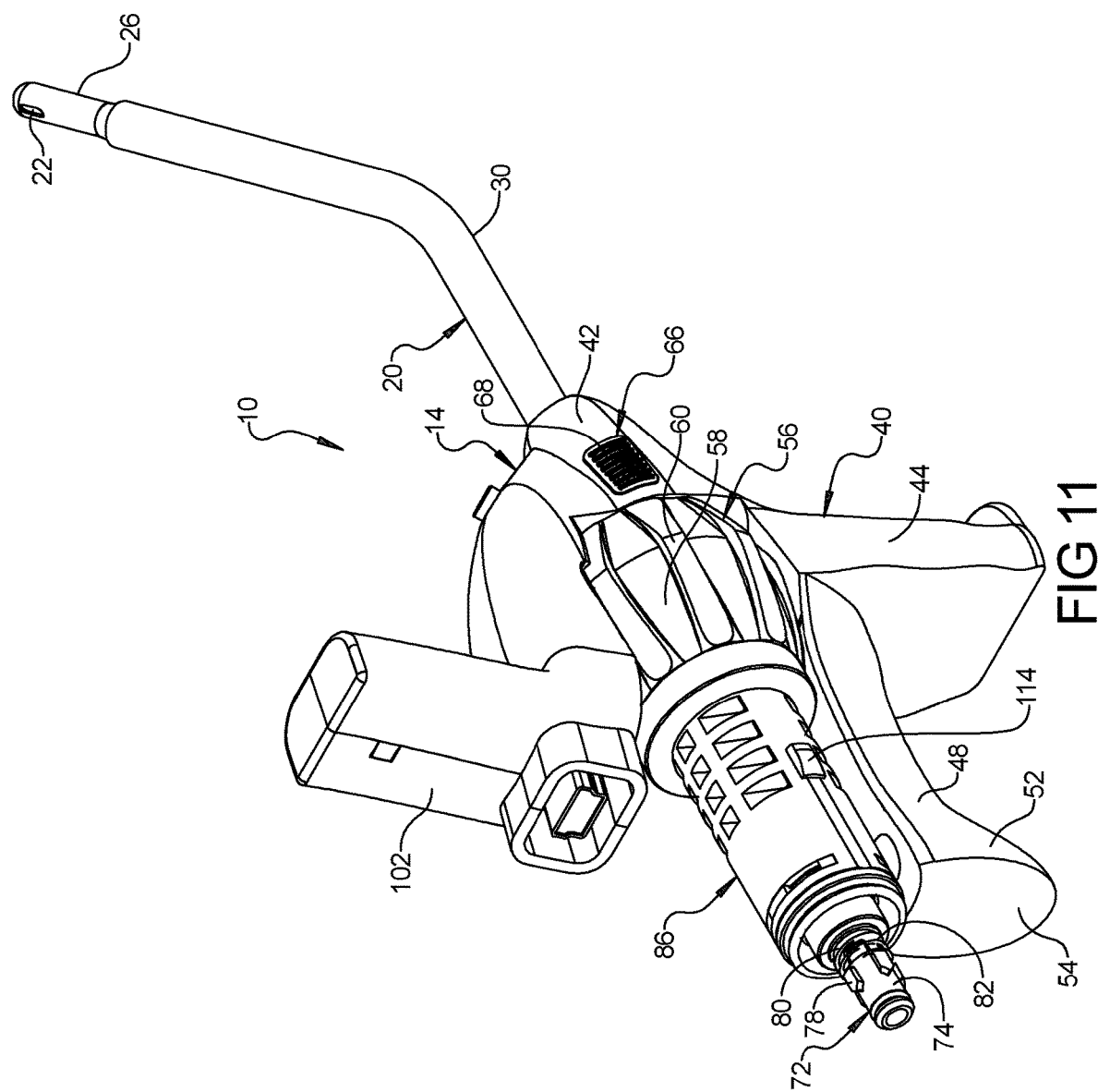
FIG. 11 is a perspective view of the surgical instrument of FIG. 10.

In another embodiment illustrated in FIGS. 10 and 11, the surgical instrument 10 may include at least one tracking element 102 coupled to the grip 40. In one embodiment, the tracking element 102 may cooperate with an integrated Pattern Recognition Optical Navigation system (as per PROFESS). In another embodiment, the tracking element 102 may be used with a computer-implemented technique for determining a coordinate transformation for surgical navigation such as disclosed in International Publication No. WO 2015/024600 to Stryker Leibinger GmbH & Co. KG. It should be appreciated that the at least one tracking element 102 is optional.

Referring to FIGS. 15-26, the drive assembly 12 may be removably connected to the cutting assembly 14. The drive assembly 12 includes the motor 16 having the rotatable drive element 18 and the housing 15 for enclosing the motor 16. The housing 15 is a generally cylindrical, elongated housing. The distal end of the housing 15 is formed with a bore 126 for receiving the proximal end of the cutting assembly 14. (Throughout this document, "distal" is understood to be away from the face of the surgeon holding the drive assembly; "proximal" is understood to mean towards the face of the surgeon.) The drive assembly 12 includes a latch or coupling assembly, generally indicated at 104, for removably coupling the housing 15 to the connecting hub 86 of the cutting assembly 14. The coupling assembly 104 includes a plurality of latch channels 106 extending axially into the housing 15. The coupling assembly 104 includes a generally ring shaped collet 108 that is secured to the housing 15. The coupling assembly 104 also includes a locking ring 110 movably disposed in the collet 108. The coupling assembly 104 includes a release button 112 integrally formed with the locking ring 110 to move the locking ring 110. The coupling assembly 104 includes one or more projections or tabs 114 on the connecting hub 86 that cooperate with the locking ring 110 to be engaged and disengaged by the locking ring 110. It should be appreciated that the release button 112 is spring loaded. It should also be appreciated that the coupling assembly 104 is similar to that disclosed in U.S. Pat. No. 7,237,990 to Deng, the entire disclosure of which is hereby incorporated by reference.

As part of the assembly of drive assembly 12, the collet 108 is attached to the housing 15. Prior to the attachment of the collet 108 to the housing 15, a coil 116 is seated in the connecting hub 86. The coil 116, which may be a wire wrap or a conductive trace formed on a flexible substrate, is the coil used to facilitate inductive signal transfer to/from a radio frequency identification device (RFID) chip 118 disposed in the connecting hub 86 (FIG. 20) between a coil seal 134 to be described and the connecting hub 86. It should be appreciated that the coil 116 and chip 118 is similar that disclosed in U.S. Pat. No. 7,237,990 to Deng.

Referring to FIGS. 22-28B, the drive assembly 12 includes an irrigation/suction connection assembly, generally indicated at 120, on the housing 15 for connection to a fluid source (not shown). In the embodiment illustrated, the irrigation/suction connection assembly 120 includes a housing 122 and an irrigation fluid connection 124 extending axially from the housing 122. The connection 124 is generally a hollow cylindrical member having a generally circular cross-sectional shape. The connection assembly 120 also includes a suction connection 126 extending axially from the housing 122 for connection to a suction source.

The drive assembly 12 includes a suction passage 128 extending axially through the housing 15 between the suction connection 126 and the drive hub 72 of the cutting assembly 14. The cutting assembly 14 includes a radial seal 130 disposed about a proximal end of the drive hub 72 to prevent fluid from exiting between the drive hub 72 and the drive element 18 when the cutting assembly 14 is coupled to the drive assembly 12. In one embodiment, the radial seal 130 may be an o-ring disposed in a groove of the drive hub 72. It should be appreciated that the suction source is connected to the suction connection 126 to aspirate fluid and tissue from the window 22 through the inner tube 24, connecting hub 86, drive hub 72, suction passage 128, and suction connection 126 to the suction source.

The drive assembly 12 also includes an irrigation passage 132 extending axially through the housing 15 between the irrigation connection 124 and the cutting assembly 14. The cutting assembly 14 includes a coil seal 134 disposed between the drive hub 72 and the connecting hub 86 to allow fluid flow between the coil seal 134 and the drive hub 72. The coil seal 134 is generally cylindrical in shape and hollow. As illustrated in FIG. 20, the coil seal 134 includes at least one or more internal protrusions 136 extending radially inwardly to engage the flange 81 on the drive hub 72 to prevent accidental disassembly of the drive hub 72 from the cutting assembly 14. In one embodiment, two opposed internal protrusions 136 extend circumferentially a predetermined distance. The coil seal 134 is formed from flexible sterilizable material. It should be appreciated that irrigation fluid flows from the irrigation passage 132 into a space between the housing 15 and the drive hub 72 and between the coil seal 134 and the drive hub 72 and into the proximal cavity 94 of the connecting hub 86.

The cutting assembly 14 may include one or more bushings 138 disposed axially between the drive hub 72 and the connecting hub 86. In one embodiment, the bushings 138 are generally planar and circular in shape. It should be appreciated that fluid flows axially past the bushings 138 and radially between the raised portions 95 in the proximal cavity 94 of the connecting hub 86. It should also be appreciated that, in one embodiment, the bushings 138 may wear due to relative rotation between the drive hub 72 and the connecting hub 86.

The cutting assembly 14 includes a radial seal 140 disposed between the manually movable member 56 and the connecting hub 86 to prevent fluid from exiting from the irrigation passage 132 between the manually movable member 56 and the connecting hub 86. The irrigation fluid is routed through the connecting hub 86 and between the inner tube 28 and outer tube 26 of the tube assembly 20 to the window 22. It should be appreciated that when the surgical instrument 10 of the present invention is employed to perform a surgical procedure, irrigating fluid is introduced into the surgical site through the irrigation connection 124 into the irrigation passage 132 and into a space between the housing 15 and the drive hub 72 and between the coil seal 134 and the drive hub 72 and into the connecting hub 86 past the bushings 138 and between the inner tube 28 and outer tube 26 of the tube assembly 20 to the window 22. It should also be appreciated that irrigation fluid may be introduced through a separate cannula that opens into the surgical site. It should further be appreciated that suction is drawn from the suction source to aspirate irrigating fluid and material from the window 22 through the inner tube 24, connecting hub 86, drive hub 72, suction passage 128, and suction connection 126 to the suction source to remove irrigating fluid and the material entrained in the irrigating fluid.

Referring to FIG. 29A, another embodiment, according to the present invention of the surgical instrument 10 is shown. In this embodiment, the cutting assembly 14 includes the tube assembly 20 having a two tube configuration of the inner tube 28 and the outer tube 26. The inner tube 28 is rotatable and connected to the drive hub 72. The outer tube 26 is also rotatable and connected to the manually movable member 56. It should be appreciated that, in the embodiment illustrated, the tube assembly 20 has a straight two tube configuration, but may be used with an angled tube assembly 20 having a bend 29. It should also be appreciated that the tube assembly 20 includes the cutting window 22 and the tube assembly 20 is connected to the grip 40 of the cutting assembly 14, which may be the disposable portion of the surgical instrument 10. It should also be appreciated that the covering tube is not included in the two tube configuration.

Figure 29B:
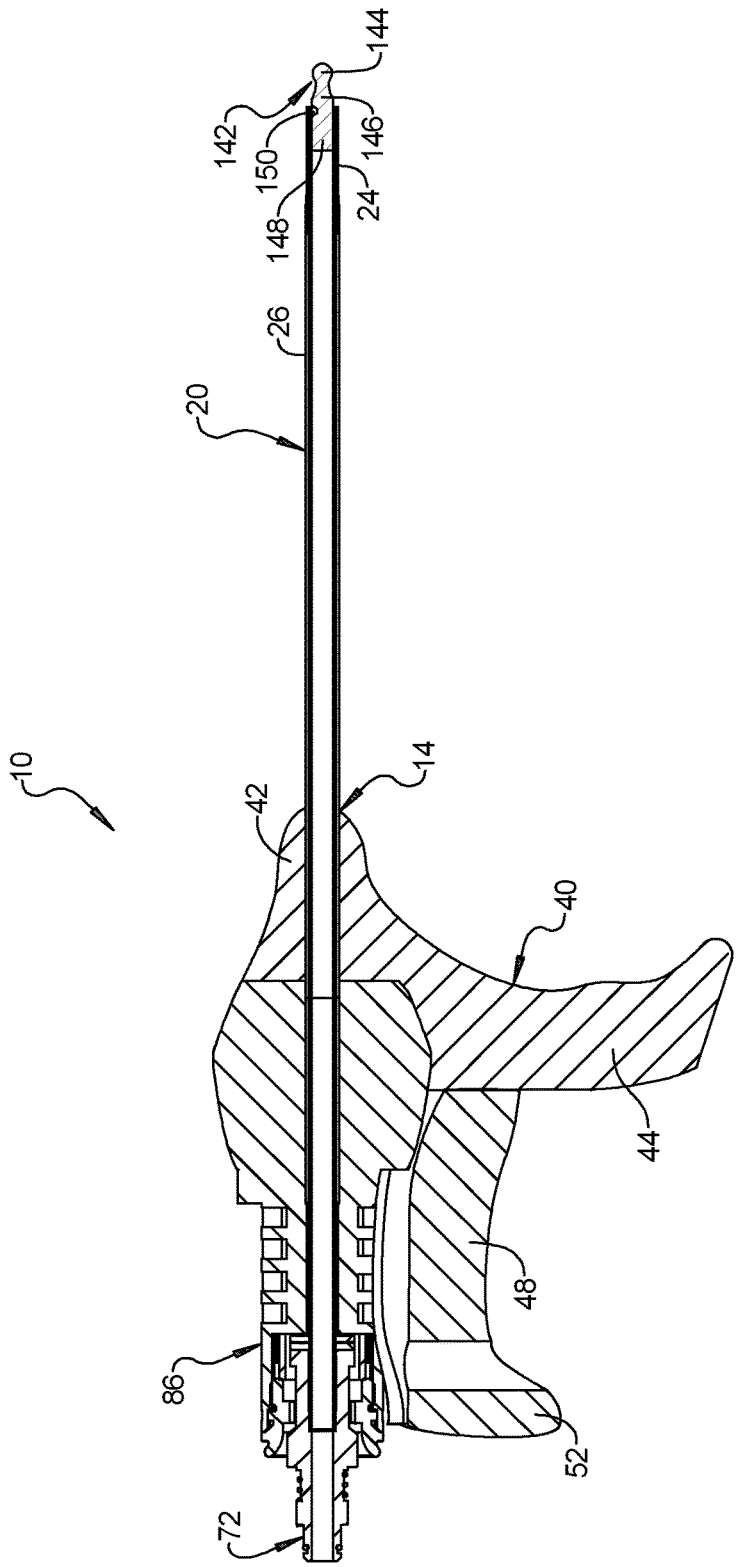
FIG. 29B is an elevational sectional view of a cutting assembly according to another exemplary embodiment of the present disclosure with the cutting assembly having a rotatable end effector.

Referring to FIG. 29B, yet another embodiment, according to the present invention of the surgical instrument 10 is shown. In this embodiment, the cutting assembly 14 includes the tube assembly 20 having a two tube configuration of the inner tube 28 and the outer tube 26. The tube assembly 20 is connected to the grip 40 of the cutting assembly 14, which may be the disposable portion of the surgical instrument 10. The inner tube 28 is rotatable and connected to the drive hub 72. The outer tube 26 is fixed and connected to the grip 40. The cutting assembly 14 also includes a rotatable end effector, generally indicated at 142, such as a bur. The rotatable end effector 142 includes a head 144 at a distal end thereof and a shaft 146 extending from the head 144 to a proximal end coupled to the inner tube 28. The head 144 is generally spherical in shape, but may be any suitable shape. The head 144 may be fluted or coated with a diamond grit to enable cutting of bone. The shaft 146 is generally cylindrical and circular in shape, but may be any suitable shape. The tube assembly 20 includes a distal bearing 148 disposed in the distal end of the inner tube 28 and the shaft 146 is coupled to the distal bearing 148. The shaft 146 may also include a notch 150 extending radially and circumferentially for suction. It should be appreciated that other end effectors are contemplated other than rotatable end effectors such as any rotatable cutting element or tool. It should also be appreciated that the tube assembly 20 has a straight two tube configuration, but may be used with an angled tube assembly 20 having a bend 29. It should further be appreciated that, in this embodiment, there is no rotatable wheel.

Figure 31:
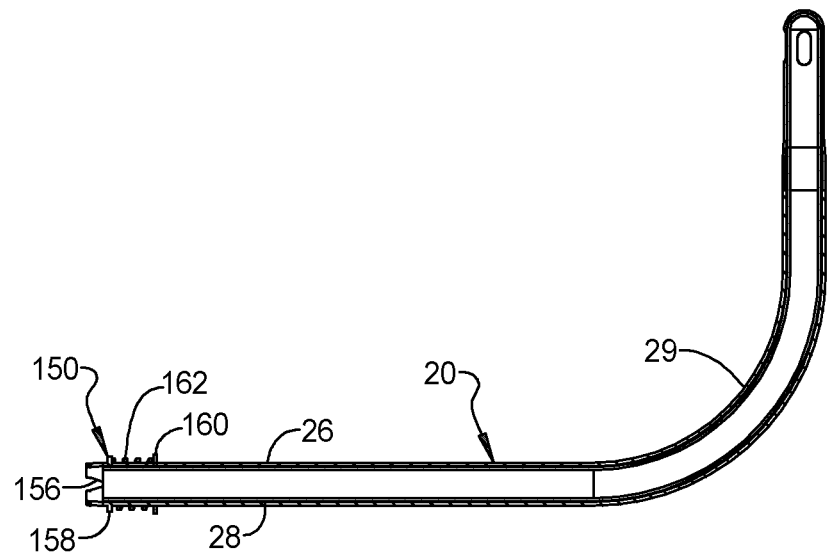
FIG. 31 is a sectional view of the tube assembly having inner and outer tubes.
Figure 32:
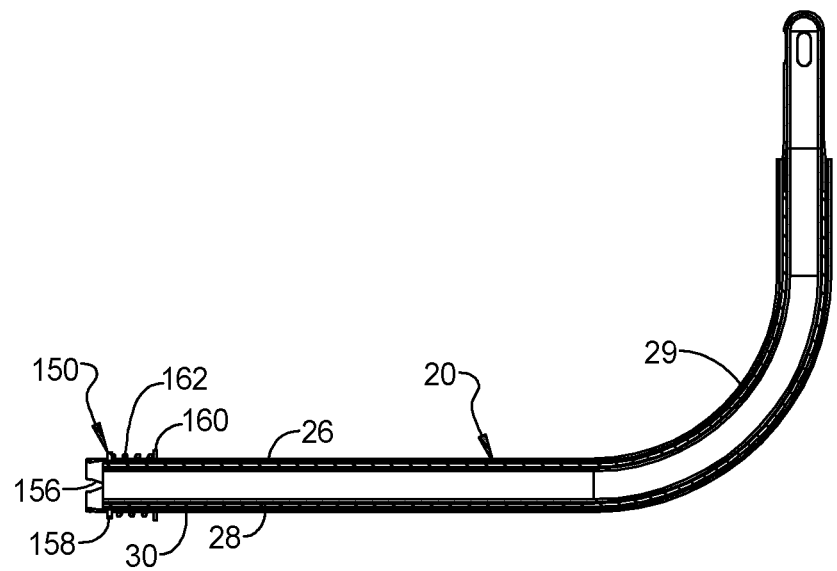
FIG. 32 is a sectional view of the tube assembly having inner, outer, and covering tubes.
Figure 33:
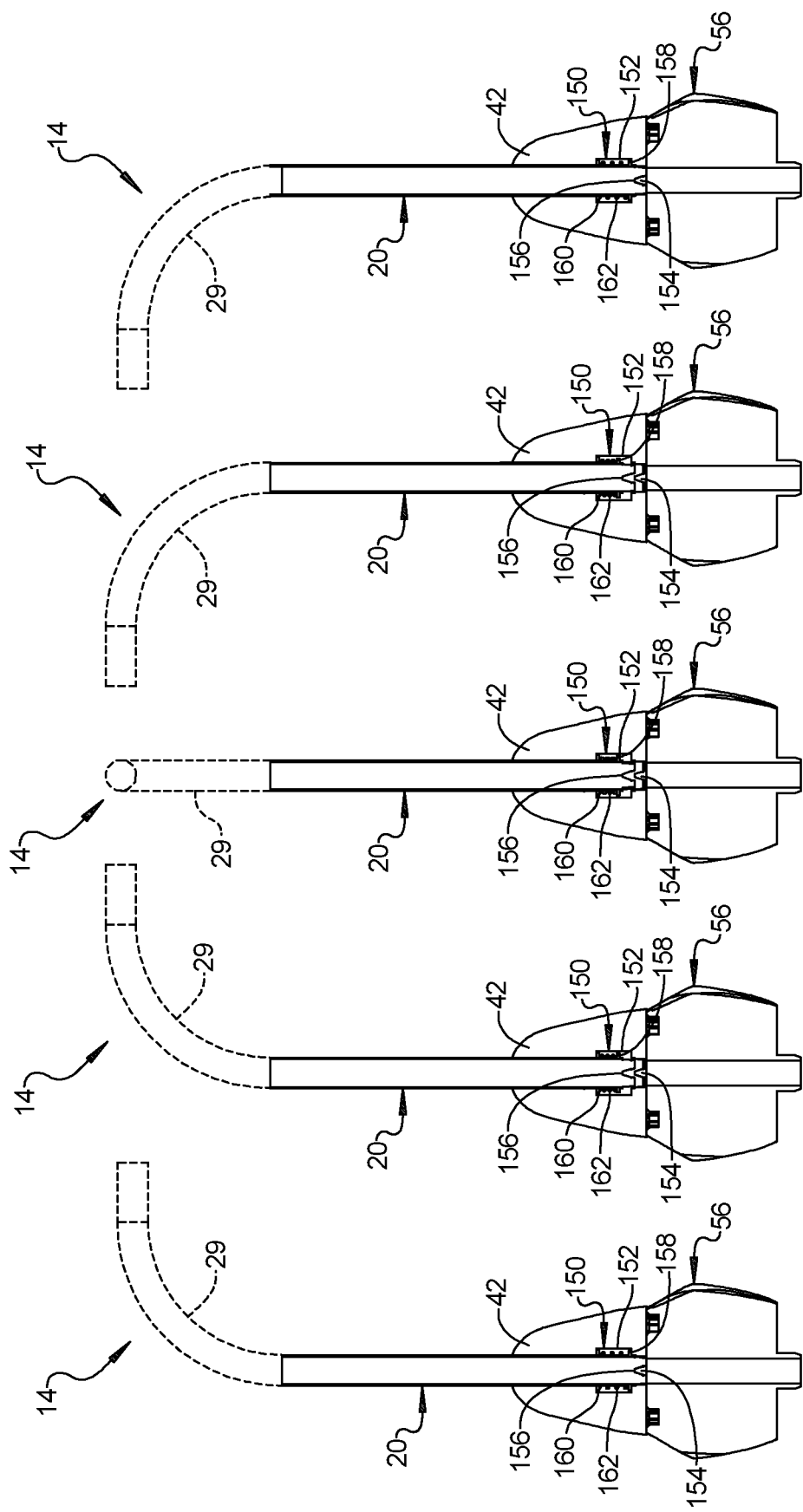
FIGS. 33A-E are fragmentary views the surgical instrument of FIG. 30 illustrating the repositioning of the tube assembly.

Referring to FIGS. 30-32, yet other embodiments, according to the present invention of the surgical instrument 10 is shown. These embodiments may also be used where there is no bend and no rotatable wheel to simply reorient the cutting window 22. In these embodiments, the cutting assembly 14 includes the tube assembly 20 having bent tube configuration. In the embodiment illustrated in FIG. 31, the tube assembly 20 has a two tube configuration of the inner tube 28 and the outer tube 26. The outer tube 26 has the bend 29 therein between the proximal end and distal end. The inner tube 28 is rotatable and connected to the drive hub 72 (not shown in this figure). The outer tube 26 is connected to the nose portion 42 of the grip 40. The cutting assembly 14 includes a relocation assembly, generally indicated at 150, that allows the surgeon to relocate the bend 29 in a plurality of orientations. In one embodiment, the bend 29 is relocated to four different orientations at ninety degrees to each other, e.g., 12 o'clock (FIG. 33C), 3 o'clock (FIGS. 33A and 33B), 6 o'clock (opposite FIG. 33C), or 9 o'clock (FIGS. 33D and 33E).

In the embodiment illustrated in FIG. 32, the tube assembly 20 has a three tube configuration of the inner tube 28, the outer tube 26, and the covering tube 30. The covering tube 30 has the bend 29 therein between the proximal end and distal end. The inner tube 28 is rotatable and connected to the drive hub 72 (not shown in this figure). The outer tube 26 is also rotatable and connected to the manually movable member 56. The covering tube 30 is connected to the nose portion 42 of the grip 40. The cutting assembly 14 includes the relocation assembly 150 that allows the surgeon to relocate the bend 29 in a plurality of orientations. In one embodiment, the bend 29 is relocated to four different orientations at ninety degrees to each other, e.g., 12, 3, 6, or 9 o'clock. It should be appreciated that, in one embodiment of a two tube configuration, the inner tube 28 has a flexible region corresponding to the bend 29 in the outer tube 26. It should also be appreciated that, in another embodiment of a three tube configuration, both the inner tube 28 and outer tube 26 have a flexible region corresponding to the bend 29 in the covering tube 30.

Referring to FIGS. 30-33E, the relocation assembly 150 includes a cavity 152 in the nose portion 42 of the grip 40 distal to the aperture 43. The relocation assembly 150 includes a plurality of projections 154 extending axially and radially and disposed circumferentially about the aperture 43. In one embodiment, the projections 154 are spaced ninety degrees to each other about the aperture 43.

The relocation assembly 150 also includes the outer most tube, either the outer tube 28 (FIG. 31) or the covering tube 30 (FIG. 32) to have a plurality of recesses 156 extending axially into the distal end and disposed circumferentially thereabout. Because the grip 40 is fixed to the cutting assembly 14, the recesses 156 allow the outer most tube to be re-orientated relative to different orientations of the hand of the user. In one embodiment, the recesses 156 are generally pentagonal in shape and are spaced ninety degrees to each other. The relocation assembly 150 includes a flange or ring 158 on the outer tube 28 or the covering tube 30. The relocation assembly 150 also includes a biasing assembly having a floating washer 160 disposed in the cavity 152 of the nose portion 42 and about the outer tube 28 or the covering tube 30. The biasing assembly also includes a spring 162 disposed in the cavity 152 of the nose portion 42 and about the outer tube 28 or the covering tube 30 between the ring 158 and floating washer 160. It should be appreciated that the projections 154 and recesses 156 are shaped to allow easy sitting and self-guiding. It should also be appreciated that the nose portion 42 may be molded such that it is a two-piece assembly with the finger portion 44, intermediate portion 48, web portion 52, and half the nose portion 42 as one molded piece and a top cap of the nose portion 42 (may include tracking element 102) as another molded piece to allow the relocation assembly 150 to be assembled.

Referring to FIGS. 33A-33E, in operation of the relocation assembly 150, the operator grips the outer tube 28 (FIG. 31) or the covering tube 30 (FIG. 32) close to the nose portion 42 of the grip 40 and pulls axially. The ring 158 moves axially and compresses the spring 162. The recesses 156 disengage the projections 154. The operator then rotates the outer tube 28 (FIG. 31) or the covering tube 30 (FIG. 32) ninety degrees. The operator releases the outer tube 28 (FIG. 31) or the covering tube 30 (FIG. 32) and the spring 162 expands and forces the recesses 156 to engage the projections 154 to lock back in position. It should be appreciated that FIGS. 33A-33E illustrate the reorientation.

The present disclosure further provides methods for gripping a cutting assembly 14 with at least a portion of a hand H of a user. In one exemplary method, the cutting assembly 14 includes a tube assembly 20 having an inner tube 28 rotatably disposed within an outer tube 26, a grip 40 coupled to the tube assembly 20 and comprising a finger portion 44 and a web portion 52, and a manually movable member 56 coupled to the outer tube 26 of the tube assembly 20. The finger portion 44 of the grip 40 is engaged with a finger of the hand. The manually movable member 56 is engaged with the finger, a thumb TH, or an index finger IF of the hand. The web portion 52 of the grip 40 is engaged with a web W disposed between the thumb TH and the index finger IF of the hand. The manually movable member 56 is moved with the thumb TH or the index finger IF to rotate the outer tube 26 of the tube assembly 20 while the web W of the hand H remains engaged with the web portion 52 and the finger of the hand H remains engaged with the finger portion 44. A drive assembly 12 comprising a motor 16 may be provided, and the drive assembly 12 may be removably coupled to the cutting assembly 14.

According to another exemplary method, for gripping a cutting assembly 14 including an inner tube 28 and an outer tube 26 with a window 22 at a distal end adapted to be applied to a surgical site of a patient, a grip 40 adapted to be engaged by a least a portion of a hand of a user and supporting the inner tube 28 and the outer tube 26, wherein the grip 40 includes a nose portion 42 having an aperture 43 extending axially therethrough to allow the inner tube 28 and the outer tube 26 to extend axially therethrough and a finger portion 44 extending from the nose portion 42 to support a finger of the hand H, and a manually movable member 56 coupled to the outer tube 26 and located axially along the grip 40 within reach of at least one finger or thumb of the user when the hand H is engaged with the grip 40. The method includes the steps of placing a finger of the hand H on the finger portion 44, placing a thumb or at least another finger of the hand H different from the finger accommodated by the finger portion 44 on the manually movable member 56, and placing a web of the hand H disposed between the thumb and index finger of the hand H on the web portion 52. The method also includes the steps of moving the manually movable member 56 with the thumb or the at least another finger to rotate the window 22 of the outer tube 26 relative to a longitudinal axis of the outer tube 26 when the hand H is engaged with the grip 40. It should be appreciated that, in one embodiment of a shaver, the inner tube 28 rotates clockwise then counterclockwise in an oscillating manner when resecting tissue.

Accordingly, the surgical instrument 10, in certain embodiments, provides a more comfortable grip and easy window rotation mechanism for reorientating a tube window 22 on the fly to perform a surgical task. The surgical instrument 10 of the present invention includes a manually movable member 56 connected to a grip 40 that may be disposed on a disposable portion of the surgical instrument 10. The surgical instrument 10 may cut and aspirate tissue as per current shaver systems, utilizing suction, irrigation, and motor rotation and the cutting window 22 is turned to re-orientate the window 22. It should be appreciated that, in another embodiment, the surgical instrument 10 may be used with the surgical tools or be a dedicated tool or instrument.

It will be further appreciated that the terms "include," "includes," and "including" have the same meaning as the terms "comprise," "comprises," and "comprising."

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

Embodiments of the disclosure may be described with reference to the following exemplary clauses:

Clause 1—A surgical instrument for use on a patient, the surgical instrument comprising: a drive assembly including a motor having a rotatable drive element; a cutting assembly configured to be removably coupled to the drive element, the cutting assembly including a plurality of tubes extending axially with a window at a distal end of at least two of the tubes adapted to be applied to a surgical site of a patient, one of the tubes being stationary and another of the tubes being rotatable relative to the one of the tubes, a grip adapted to be engaged by a least a portion of a palm of a hand of a user and supporting the one of the tubes, and a manually movable member coupled to the one of the tubes and located axially along the grip within reach of a thumb or at least one finger of the hand of the user when the hand is engaged with the grip to allow the at least one finger to rotate the window of the one of the tubes relative to a longitudinal axis of the tubes.

Clause 2—A surgical instrument as set forth in clause 1 wherein the grip comprises a nose portion having an aperture extending axially therethrough to allow the at least one of the tubes to extend axially therethrough.

Clause 3—A surgical instrument as set forth in clause 2 wherein the grip further comprises a finger portion extending from the nose portion to support a finger of the hand different from the at least one finger.

Clause 4—A surgical instrument as set forth in clause 3 wherein the finger portion extends from the nose portion at an angle between at least perpendicular and an obtuse angle relative to the nose portion.

Clause 5—A surgical instrument as set forth in clause 3 wherein the grip further comprises an intermediate portion extending axially from the finger portion towards the drive assembly.

Clause 6—A surgical instrument as set forth in clause 5 wherein the grip includes a web portion extending from the intermediate portion and apart from the finger portion to engage a web disposed between a thumb and an index finger of the hand.

Clause 7—A surgical instrument as set forth in clause 6 wherein a position of the web portion is adjustable relative to a position of the finger portion.

Clause 8—A surgical instrument as set forth in clause 1 wherein the tubes comprise an outer tube coupled to the manually movable member and an inner tube coupled to the drive element and being rotatable by the drive element relative to the outer tube.

Clause 9—A surgical instrument as set forth in clause 8 wherein the outer tube comprises an outer opening forming the window.

Clause 10—A surgical instrument as set forth in clause 9 wherein the inner tube has an inner opening aligned with the outer opening.

Clause 11—A surgical instrument as set forth in clause 8 wherein the manually movable member comprises a rotatable wheel coupled to the outer tube to allow the at least one finger of the hand of the user to rotate the outer tube relative to the longitudinal axis.

Clause 12—A surgical instrument as set forth in clause 11 wherein the rotatable wheel is disposed about and attached to the outer tube, wherein the rotatable wheel includes a projection extending axially.

Clause 13—A surgical instrument as set forth in clause 12 further comprising a drive hub disposed about a proximal end of the inner tube to allow the inner tube to be connected to the drive element for rotation of the inner tube about the longitudinal axis.

Clause 14—A surgical instrument as set forth in clause 13 further comprising a connecting hub disposed about the inner tube and the drive hub for connection to the drive assembly.

Clause 15—A surgical instrument as set forth in clause 14 wherein the connecting hub includes a distal cavity extending axially therein to receive the projection.

Clause 16—A surgical instrument as set forth in clause 6 wherein the web portion and the finger portion each comprise a length extending away from the tubes, wherein the length of the finger portion is greater than the length of the web portion.

Clause 17—A surgical instrument as set forth in clause 8 wherein the tubes include a covering tube disposed about the outer tube and being coupled to the grip to be stationary relative to the grip.

Clause 18—A surgical instrument as set forth in clause 17 wherein the covering tube has a bend disposed between the grip and a distal end thereof.

Clause 19—A surgical instrument as set forth in clause 1 wherein the grip is separable from at least one of the tubes.

Clause 20—A surgical instrument as set forth in clause 16 wherein the drive assembly includes a housing for enclosing the motor and a latch assembly for removably coupling the housing to the connecting hub of the cutting assembly.

Clause 21—A surgical instrument as set forth in clause 20 wherein the drive assembly includes an irrigation connection on the housing for connection to a fluid source.

Clause 22—A surgical instrument as set forth in clause 21 wherein the drive assembly includes an irrigation passage extending through the housing between the irrigation connection and the cutting assembly.

Clause 23—A surgical instrument as set forth in clause 22 wherein the cutting assembly includes a coil seal disposed between the drive hub and the connecting hub to allow fluid flow between the coil seal and the drive hub.

Clause 24—A surgical instrument as set forth in clause 23 wherein the coil seal includes at least one internal protrusion to engage the drive hub to prevent accidental disassembly of the drive hub from the cutting assembly.

Clause 25—A surgical instrument as set forth in clause 24 wherein the cutting assembly includes a first radial seal disposed between the manually movable member and the connecting hub to prevent fluid from exiting from the irrigation passage between the manually movable member and the connecting hub.

Clause 26—A surgical instrument as set forth in clause 24 wherein the irrigation passage is routed past the coil seal and through the connecting hub between the connecting hub and the tubes.

Clause 27—A surgical instrument as set forth in clause 25 wherein the cutting assembly includes a second radial seal disposed about a proximal end of the drive hub to prevent fluid from exiting between the drive hub and the drive element when the cutting assembly is coupled to the drive assembly.

Clause 28—A surgical instrument as set forth in clause 27 wherein the cutting assembly includes at least one bushing disposed axially between the drive hub and the connecting hub.

Clause 29—A surgical instrument as set forth in clause 27 wherein the connecting hub includes at least one aperture extending radially through a proximal end thereof to engage the coil seal.

Clause 30—A surgical instrument as set forth in clause 28 wherein the connecting hub includes a proximal cavity extending axially therein and at least one raised area extending axially and radially from an axial end of the proximal cavity to allow fluid flow from the at least one aperture into the proximal cavity and between the bushing and the connecting hub.

Clause 31—A surgical instrument as set forth in clause 30 wherein the drive assembly includes a suction connection on the housing for connection to a suction source.

Clause 32—A surgical instrument as set forth in clause 31 wherein the drive assembly includes a suction passage extending through the housing between the suction connection and the cutting assembly.

Clause 33—A surgical instrument as set forth in clause 20 wherein the latch assembly comprises a plurality of latch channels extending axially into the housing.

Clause 34—A surgical instrument as set forth in clause 23 including a radio frequency identification (RFID) disposed between the coil seal and the connecting hub.

Clause 35—A surgical instrument as set forth in clause 23 including a cutter drive spring disposed about the drive hub.

Clause 36—A surgical instrument as set forth in clause 18 including a relocation assembly to allow the user to relocate a bend in one of the tubes to one or more different orientations.

Clause 37—A surgical instrument as set forth in clause 36 wherein the relocation assembly includes a plurality of recesses in a distal end of the one of the tubes and a plurality of projections in the aperture of the nose portion, the recesses and the projections matingly engaging and disengaging each other.

Clause 38—A surgical instrument as set forth in clause 37 wherein the relocation assembly includes a cavity in the nose portion, a ring disposed about and fixed to the one of the tubes and disposed in the cavity, a floating washer disposed about the one of the tubes and spaced axially from the ring and disposed in the cavity, and a spring disposed about the one of the tubes and spaced axially between the floating washer and the ring and disposed in the cavity.

Clause 40—A surgical instrument as set forth in clause 11 including a locking assembly cooperating with the grip to lock the rotatable wheel in place relative to the grip.

Clause 41—A surgical instrument as set forth in clause 40 wherein the locking assembly comprises one or more movable members having a pin at one axial end and one or more recesses disposed circumferentially about the rotatable wheel to receive the pin.

Clause 42—A cutting assembly for a surgical instrument for use on a patient, the cutting assembly being configured to be coupled to a drive assembly including a motor having a rotatable drive element enclosed in a housing and, the cutting assembly comprising: a plurality of tubes, one of the tubes being a rotatable inner tube adapted to be rotated by the drive element and another of the tubes being a rotatable outer tube disposed over the inner tube with a window at a distal end adapted to be applied to a surgical site of a patient; a grip supporting the outer tube, the grip configured to be engaged by a least a portion of a palm of a hand of a user; and a manually movable member coupled to the outer tube and located axially along the grip within reach of at least one finger of the hand of the user when the portion of the hand is engaged with the grip to allow the at least one finger to rotate the window of the outer tube relative to a longitudinal axis of the outer tube.

Clause 43—A cutting assembly as set forth in clause 42 wherein the grip comprise a nose portion having an aperture extending axially therethrough to allow the outer tube to extend axially therefrom, and a finger portion extending from the nose portion to support a finger of the hand different from the at least one finger.

Clause 44—A cutting assembly as set forth in clause 43 wherein the finger portion extends from the nose portion at an angle between at least perpendicular and an obtuse angle relative to the nose portion.

Clause 45—A cutting assembly as set forth in clause 43 wherein the grip further comprises an intermediate portion extending axially from the finger portion, and a web portion extending from the intermediate portion and spaced part from the finger portion to support a web disposed between a thumb and an index finger of the hand.

Clause 46—A cutting assembly as set forth in clause 43 wherein the tubes include a covering tube disposed about the outer tube and being coupled to the grip to be stationary relative to the grip.

Clause 47—A cutting assembly as set forth in clause 46 wherein one of the covering tube and the outer tube has a bend disposed between the grip and a distal end thereof.

Clause 48—A cutting assembly as set forth in clause 45 wherein the manually movable member is within reach of an index finger or thumb of the hand when the web and a finger of the hand different from the index finger are engaged with the web portion and the finger portion, respectively.

Clause 49—A cutting assembly as set forth in clause 45 wherein the web portion and the finger portion each comprise a length extending away from the outer tube, wherein the length of the finger portion is larger than the length of the web portion.

Clause 50—A cutting assembly as set forth in clause 42 wherein the finger portion defines a front surface and sized such that the front surface accommodates at least one finger of the hand of the user.

Clause 51—A cutting assembly as set forth in clause 42 wherein the cutting assembly is free of a motor.

Clause 52—A cutting assembly as set forth in clause 42 further comprising at least one tracking element coupled to the grip.

Clause 53—A cutting assembly as set forth in clause 42 wherein the manually movable member is located axially along the grip and within at least forty percent of a length from the finger portion.

Clause 54—A cutting assembly as set forth in clause 47 including a relocation assembly to allow the user to relocate a bend in one of the tubes to one or more different orientations.

Clause 55—A cutting assembly as set forth in clause 48 wherein the relocation assembly includes a plurality of recesses in a distal end of the one of the tubes and a plurality of projections in the aperture of the nose portion, the recesses and the projections matingly engaging and disengaging each other.

Clause 56—A cutting assembly as set forth in clause 55 wherein the relocation assembly includes a cavity in the nose portion, a ring disposed about and fixed to the one of the tubes and disposed in the cavity, a floating washer disposed about the one of the tubes and spaced axially from the ring and disposed in the cavity, and a spring disposed about the one of the tubes and spaced axially between the floating washer and the ring and disposed in the cavity.

Clause 57—A cutting assembly as set forth in clause 42 including a locking assembly cooperating with the grip to lock the manually movable member in place relative to the grip.

Clause 58—A cutting assembly as set forth in clause 51 wherein the locking assembly comprises one or more movable members having a pin at one axial end and one or more recesses disposed circumferentially about the manually movable member to receive the pin.

Clause 59—A surgical instrument for use on a patient comprising a cutting assembly and a drive assembly, the drive assembly being configured to be coupled to the cutting assembly, the drive assembly comprising: a motor having a rotatable drive element; a housing for enclosing the motor; a latch assembly cooperating with the housing for removably coupling the housing to the cutting assembly; an irrigation connection on the housing for connection to a fluid source; an irrigation passage extending through the housing between the irrigation connection and the cutting assembly; a suction connection on the housing for connection to a suction source; and a suction passage extending through the housing between the suction connection and the cutting assembly.

Clause 60—A surgical instrument as set forth in clause 59 including a coil seal adapted to be disposed between a drive hub and a connecting hub of the cutting assembly to allow fluid flow between the coil seal and the drive hub.

Clause 61—A surgical instrument as set forth in clause 60 wherein the coil seal includes at least one internal protrusion adapted to engage the drive hub to prevent accidental disassembly of the drive hub from the cutting assembly.

Clause 62—A surgical instrument as set forth in clause 60 including a radial seal adapted to be disposed between a manually movable member of the cutting assembly and the connecting hub to prevent fluid from exiting the irrigation passage between the manually movable member and the connecting hub.

Clause 63—A surgical instrument as set forth in clause 60 wherein the irrigation passage is routed past the coil seal and through the connecting hub between the connecting hub and at least one tube of the cutting assembly.

Clause 64—A surgical instrument as set forth in clause 63 including a radial seal adapted to be disposed about a proximal end of the drive hub to prevent fluid from exiting between the drive hub and the drive element when the cutting assembly is coupled to the drive assembly.

Clause 65—A surgical instrument as set forth in clause 63 including a bushing adapted to be disposed axially between the drive hub and the connecting hub to prevent fluid in the irrigation passage from exiting radially between the drive hub and the connecting hub.

Clause 66—A surgical instrument comprising: a cutting assembly including a plurality of tubes extending axially with a window at a distal end adapted to be applied to a surgical site of a patient, a grip adapted to be engaged by a least a portion of a palm of a hand of a user and supporting the tubes, and a manually movable member coupled to at least one of the tubes and located axially along the grip within reach of a thumb or at least one finger of the hand of the user when the hand is engaged with the grip to allow the at least one finger to rotate the window of the at least one of the tubes relative to a longitudinal axis of the tubes; and a drive assembly including a motor having a rotatable drive element, a housing for enclosing the motor, a latch assembly cooperating with the housing for removably coupling the housing to the cutting assembly, an irrigation connection on the housing for connection to a fluid source, an irrigation passage extending through the housing between the irrigation connection and the at least one tube to the distal end thereof, a suction connection on the housing for connection to a suction source, and a suction passage extending from the window through the tubes and through the housing to the suction connection.

Clause 67—A cutting assembly for a surgical instrument for use on a patient, the cutting assembly being configured to be coupled to a drive assembly including a motor having a rotatable drive element enclosed in a housing and, the cutting assembly comprising: a rotatable inner member adapted to be rotated by the drive element and an outer tube disposed over the inner member; and a grip supporting the outer tube, the grip configured to be engaged by a least a portion of a palm of a hand of a user and a finger of the hand, wherein the grip comprises a nose portion having an aperture extending axially therethrough to allow the inner member to extend axially therethrough, wherein the grip further comprises a finger portion extending from the nose portion to support a finger of the hand.

Clause 68—A cutting assembly as set forth in clause 67 wherein the finger portion extends from the nose portion at an angle between at least perpendicular and an obtuse angle relative to the nose portion.

Clause 69—A cutting assembly as set forth in clause 67 wherein the grip further comprises an intermediate portion extending axially from the finger portion.

Clause 70—A cutting assembly as set forth in clause 69 wherein the grip includes a web portion extending from the intermediate portion and apart from the finger portion to engage a web disposed between a thumb and an index finger of the hand.

Clause 71—A cutting assembly as set forth in clause 70 wherein a position of the web portion is adjustable relative to a position of the finger portion.

Clause 72—A cutting assembly as set forth in clause 67 wherein the outer tube includes a cutting window at a distal end adapted to be applied to a surgical site of a patient.

Clause 73—A cutting assembly as set forth in clause 67 including a bur coupled to a distal end of the inner member.

Clause 74—A method for gripping a cutting assembly including an inner tube and an outer tube with a window at a distal end adapted to be applied to a surgical site of a patient, a grip adapted to be engaged by a least a portion of a hand of a user and supporting the inner tube and the outer tube, wherein the grip includes a nose portion having an aperture extending axially therethrough to allow the inner tube and outer tube to extend axially therethrough and a finger portion extending from the nose portion to support a finger of the hand, and a manually movable member coupled to the outer tube and located axially along the grip within reach of at least one finger or thumb of the hand of the user when the hand is engaged with the grip, the method comprising the steps of: placing a finger of the hand on the finger portion; placing a thumb or at least another finger of the hand different from the finger accommodated by the finger portion on the manually movable member; placing a web of the hand disposed between the thumb and index finger of the hand on the web portion; and moving the manually movable member with the thumb or the at least another finger to rotate the window of the outer tube relative to a longitudinal axis of the outer tube when the hand is engaged with the grip.

Clause 75—A surgical instrument comprising: a drive assembly comprising a motor having a rotatable drive element, and a housing coupled to said motor; a cutting assembly comprising an inner tube adapted to be rotated by said drive assembly, an outer tube disposed over said inner tube, a drive hub for coupling said inner tube to said rotatable drive element, a connecting hub for coupling said cutting assembly to said drive assembly, and a manually movable member coupled to said cutting assembly and adapted to be rotated by the user to rotate said outer tube; an irrigation connection disposed on said housing for connection to a fluid source; an irrigation passage extending through said housing between said irrigation connection and said cutting assembly; a suction connection disposed on said housing for connection to a suction source; a suction passage extending through said housing between said suction connection and said cutting assembly; a coil seal disposed between said drive hub and said connecting hub of the cutting assembly to allow fluid flow between said coil seal and said drive hub; and a radial seal disposed between said manually movable member and said connecting hub to prevent fluid from exiting said irrigation passage between said manually movable member and said connecting hub.

What is claimed is:
1. A cutting assembly for a surgical instrument having a drive assembly including a motor, said cutting assembly being configured to be removably coupled to the drive assembly of the surgical instrument, said cutting assembly comprising:

a tube assembly comprising a longitudinal axis defined between a distal end opposite a proximal end, a cutting window at said distal end and adapted to be applied to a surgical site of a patient, an inner tube adapted to be rotated by the drive assembly and comprising an inner tube aperture, and an outer tube disposed over said inner tube and comprising an outer tube aperture with said inner tube and outer tube apertures defining said cutting window of said tube assembly;

a grip coupled to said tube assembly and configured to be engaged by a portion of a hand of a user with the hand comprising a thumb, a plurality of fingers including an index finger and a secondary finger, a web disposed between the thumb and the index finger, and a palm;

a connecting hub coupled to said tube assembly and configured to be removably coupled to the drive assembly of the surgical instrument; and a manually movable member coupled to said outer tube and adapted to be rotated by the user to rotate said outer tube aperture about said longitudinal axis, wherein said manually movable member is adapted to be rotated with the index finger or the thumb of the hand while said grip is engaged by the web of the hand, wherein said grip further comprises a nose portion having an aperture extending axially therethrough to allow said outer tube to extend axially therefrom, a finger portion extending from said nose portion and adapted to be engaged by the index finger or the secondary finger of the hand, a web portion adapted to be engaged by the web of the hand, and an intermediate portion coupled to said finger portion and said web portion, wherein said intermediate portion is curved and each of said finger portion and said web portion extend away from said intermediate portion to collectively define a cavity sized to accommodate the web of the hand, and wherein said manually movable member is axially positioned between said nose portion and said connecting hub.

2. The cutting assembly of claim 1, wherein said manually movable member is adapted to be rotated with the index finger of the hand while said finger portion is engaged by the secondary finger of the hand and said web portion is engaged by the web of the hand.

3. The cutting assembly of claim 1, wherein said manually movable member is adapted to be rotated with both the index finger and the thumb of the hand while said finger portion is engaged by the secondary finger of the hand and said web portion is engaged by the web of the hand.

4. The cutting assembly of claim 1, wherein said finger portion is configured to be engaged by the index finger or the secondary finger of the hand and said grip is configured to be engaged by the web of the hand so as to provide opposing forces to said grip without the palm of the hand engaging said grip.

5. The cutting assembly of claim 1, wherein each of said finger portion and said web portion extend away from said intermediate portion in a direction opposite said movable member to define a generally U-shaped configuration of said grip.

6. The cutting assembly of claim 1, wherein said outer tube has a bend disposed between said distal and proximal ends of said tube assembly, said inner tube comprising a flexible region corresponding to said bend of said outer tube such that said inner tube is adapted to rotate relative to said bent outer tube.

7. The cutting assembly of claim 1, wherein said tube assembly further comprises a covering tube disposed about said outer tube and being coupled to and stationary relative to said grip with said inner and outer tubes adapted to be rotated relative to said covering tube.

8. The cutting assembly of claim 1, further comprising a locking assembly coupled to said nose portion of said grip and configured to lock said manually movable member from rotation relative to said grip, said locking assembly adapted to be engaged by the index finger or the thumb of the hand while said grip is engaged by the web of the hand.

9. The cutting assembly of claim 1, wherein said tube assembly, said grip, and said manually movable member collectively form a disposable portion of the surgical instrument.

10. The cutting assembly of claim 1, wherein each of said finger portion and said web portion extend away from said intermediate portion by respective lengths, wherein said length of said finger portion is greater than said length of said web portion.

11. The cutting assembly of claim 1, wherein said web portion is adjustable relative to a position of said finger portion.

12. A cutting assembly for a surgical instrument having a drive assembly including a motor, said cutting assembly being configured to be removably coupled to the drive assembly of the surgical instrument, said cutting assembly comprising:

a tube assembly comprising a longitudinal axis defined between a distal end opposite a proximal end, a cutting window at said distal end and adapted to be applied to a surgical site of a patient, an inner tube adapted to be rotated by the drive assembly and comprising an inner tube aperture, and an outer tube disposed over said inner tube and comprising an outer tube aperture with said inner tube and outer tube apertures defining said cutting window of said tube assembly;

a grip coupled to said tube assembly and configured to be engaged by a portion of a hand of a user with the hand comprising a thumb, a plurality of fingers including an index finger and a secondary finger, a web disposed between the thumb and the index finger, and a palm;

a connecting hub coupled to said tube assembly and configured to be removably coupled to the drive assembly of the surgical instrument; and a manually movable member coupled to said outer tube and adapted to be rotated by the user to rotate said outer tube aperture about said longitudinal axis, wherein said manually movable member is adapted to be rotated with the index finger or the thumb of the hand while said grip is engaged by the web of the hand, wherein said grip further comprises a nose portion having an aperture extending axially therethrough to allow said outer tube to extend axially therefrom, a finger portion extending from said nose portion and adapted to be engaged by the index finger or the secondary finger of the hand, a web portion adapted to be engaged by the web of the hand, and an intermediate portion coupled to said finger portion and said web portion, wherein said intermediate portion extends proximally from said finger portion to form with said nose portion an open area ledge shaped to receive said manually movable member, wherein said manually movable member comprises a gripping surface positioned radially outwardly relative to a side of said nose portion that defines said open area ledge, and wherein said manually movable member is axially positioned between said nose portion and said connecting hub.

13. The cutting assembly of claim 12, wherein said open area ledge is sized to receive at least a portion of said connecting hub.

14. The cutting assembly of claim 13, wherein said manually movable member is positioned proximal to said nose portion.

* * * * *